US012558036B2

(12) United States Patent
Krause et al.

(10) Patent No.: US 12,558,036 B2
(45) Date of Patent: Feb. 24, 2026

(54) ACUTE HEALTH EVENT MONITORING AND VERIFICATION

(71) Applicant: Medtronic, Inc., Minneapolis, MN (US)

(72) Inventors: Paul G. Krause, Mahtomedi, MN (US); Robert W. Stadler, Shoreview, MN (US); Paul J. DeGroot, Minneapolis, MN (US); Ryan D. Wyszynski, Oak Grove, MN (US); Megan Connolly, Buffalo, MN (US); Grant A. Neitzell, Loretto, MN (US); Shantanu Sarkar, Roseville, MN (US); Christopher D. Koch, Minneapolis, MN (US); Yong K. Cho, Excelsior, MN (US); Ana C. Natera, Somerville, MA (US); Kevin T. Ousdigian, Shoreview, MN (US); Wade M. Demmer, Coon Rapids, MN (US); Abhijit P. Jejurkar, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 104 days.

(21) Appl. No.: 18/549,400

(22) PCT Filed: Feb. 10, 2022

(86) PCT No.: PCT/US2022/070616
§ 371 (c)(1),
(2) Date: Sep. 7, 2023

(87) PCT Pub. No.: WO2022/192827
PCT Pub. Date: Sep. 15, 2022

(65) Prior Publication Data
US 2024/0148332 A1     May 9, 2024

Related U.S. Application Data

(60) Provisional application No. 63/182,456, filed on Apr. 30, 2021, provisional application No. 63/158,189, filed on Mar. 8, 2021.

(51) Int. Cl.
| A61B 5/07 | (2006.01) |
| A61B 5/00 | (2006.01) |
| A61B 5/11 | (2006.01) |

(52) U.S. Cl.
CPC .......... *A61B 5/7221* (2013.01); *A61B 5/1117* (2013.01); *A61B 5/686* (2013.01); *A61B 5/7282* (2013.01); *A61B 5/746* (2013.01)

(58) Field of Classification Search
CPC ..... A61B 5/7221; A61B 5/1117; A61B 5/686; A61B 5/7282; A61B 5/746; A61B 5/0022;
(Continued)

(56) References Cited

U.S. PATENT DOCUMENTS

| 3,552,386 A | 1/1971 | Horth |
| 3,598,110 A | 8/1971 | Edmark |
(Continued)

FOREIGN PATENT DOCUMENTS

| CA | 3075015 A1 | 9/2021 |
| CN | 105068486 A | 11/2015 |
(Continued)

OTHER PUBLICATIONS

"Cardiac Arrest: An Important Public Health Issue," CDC, retrieved from https://www.cdc.gov/dhdsp/docs/cardiac-arrest-infographic.pdf, on Apr. 23, 2021, 2 pp.
(Continued)

*Primary Examiner* — Masud Ahmed
(74) *Attorney, Agent, or Firm* — Shumaker & Sieffert, P.A.

(57) ABSTRACT

Devices, systems, and techniques are disclosed for verifying the occurrence of an acute health event. An example device includes communication circuitry configured to receive a communication indicative of an acute health event of a patient and memory communicatively coupled to the communication circuitry and being configured to store the indication of the acute health event. The device includes pro-
(Continued)

cessing circuitry communicatively coupled to the communication circuitry and the memory. The processing circuitry is configured to, in response to the communication, verify the acute health event and based on the verification of the acute health event, send an alert regarding the acute health event.

20 Claims, 6 Drawing Sheets

(58) Field of Classification Search
CPC ........ A61B 5/0031; A61B 5/747; A61N 1/37; A61N 1/3956; A61N 1/37282; A61N 1/362; A61N 1/37258; A61N 1/3925; G16H 10/20; G16H 20/30; G16H 50/20; G16H 40/67; G16H 10/60; G16H 20/10; G16H 40/20; G16H 40/63; G16H 50/30; G16H 50/70
See application file for complete search history.

(56) References Cited

U.S. PATENT DOCUMENTS

| | | | |
|---|---|---|---|
| 3,658,055 A | 4/1972 | Abe et al. | |
| 3,677,260 A | 7/1972 | Funfstuck et al. | |
| 3,828,768 A | 8/1974 | Douglas | |
| 3,861,387 A | 1/1975 | Lawhorn et al. | |
| 3,927,663 A | 12/1975 | Russell et al. | |
| 4,023,564 A | 5/1977 | Valiquette et al. | |
| 4,306,567 A | 12/1981 | Krasner | |
| 4,457,315 A | 7/1984 | Bennish | |
| 4,958,641 A | 9/1990 | Digby et al. | |
| 5,065,766 A | 11/1991 | Sasaki | |
| 5,217,021 A | 6/1993 | Steinhaus et al. | |
| 5,228,449 A | 7/1993 | Christ et al. | |
| 5,271,411 A | 12/1993 | Ripley et al. | |
| 5,366,487 A | 11/1994 | Adams et al. | |
| 5,404,877 A | 4/1995 | Nolan et al. | |
| 5,416,695 A | 5/1995 | Stutman et al. | |
| 5,458,123 A | 10/1995 | Unger | |
| 5,944,680 A | 8/1999 | Christopherson et al. | |
| 6,095,984 A | 8/2000 | Amana et al. | |
| 6,129,678 A | 10/2000 | Ryan et al. | |
| 6,292,687 B1 | 9/2001 | Lowell et al. | |
| 6,485,429 B2 | 11/2002 | Forstner | |
| 6,487,442 B1 | 11/2002 | Wood | |
| 6,490,478 B1 | 12/2002 | Zhang et al. | |
| 6,493,581 B2 | 12/2002 | Russell | |
| 6,609,023 B1 | 8/2003 | Fischell et al. | |
| 6,907,238 B2 | 6/2005 | Leung | |
| 6,980,112 B2 | 12/2005 | Nee | |
| 7,076,290 B2 | 7/2006 | Sheth et al. | |
| 7,092,751 B2 | 8/2006 | Erkkili | |
| 7,117,031 B2 | 10/2006 | Lohman et al. | |
| 7,194,354 B1 | 3/2007 | Oran et al. | |
| 7,212,849 B2 | 5/2007 | Zhang et al. | |
| 7,312,709 B2 | 12/2007 | Kingston | |
| 7,343,199 B2 | 3/2008 | Hatlestad et al. | |
| 7,353,179 B2 | 4/2008 | Ott et al. | |
| 7,396,330 B2 | 7/2008 | Banet et al. | |
| 7,480,529 B2 | 1/2009 | Li | |
| 7,502,498 B2 | 3/2009 | Wen et al. | |
| 7,558,623 B2 | 7/2009 | Fischell et al. | |
| 7,689,282 B2 | 3/2010 | Zhang et al. | |
| 7,702,382 B2 | 4/2010 | Xue | |
| 7,715,905 B2 | 5/2010 | Kurzweil et al. | |
| 7,733,224 B2 | 6/2010 | Tran | |
| 7,801,596 B2 | 9/2010 | Fischell et al. | |
| 7,840,277 B2 | 11/2010 | Matos | |
| 7,844,323 B2 | 11/2010 | Fischell et al. | |
| 7,846,106 B2 | 12/2010 | Andrews et al. | |
| 7,860,559 B2 | 12/2010 | Fischell et al. | |
| 7,889,092 B2 | 2/2011 | Volk et al. | |
| 7,894,883 B2 | 2/2011 | Gunderson et al. | |

| | | | |
|---|---|---|---|
| 7,991,460 B2 | 8/2011 | Fischell et al. | |
| 8,002,701 B2 | 8/2011 | John et al. | |
| 8,073,536 B2 | 12/2011 | Gunderson et al. | |
| 8,073,537 B2 | 12/2011 | Gunderson et al. | |
| 8,108,036 B2 | 1/2012 | Tran | |
| 8,112,153 B2 | 2/2012 | Giftakis et al. | |
| 8,170,609 B2 | 5/2012 | Hedtke et al. | |
| 8,170,653 B2 | 5/2012 | Fischell et al. | |
| 8,204,580 B2 | 6/2012 | Kurzweil et al. | |
| 8,214,043 B2 | 7/2012 | Matos | |
| 8,224,430 B2 | 7/2012 | Fischell et al. | |
| 8,239,020 B2 | 8/2012 | Zhang et al. | |
| 8,265,740 B2 | 9/2012 | Fischell et al. | |
| 8,265,751 B2 | 9/2012 | Zhang et al. | |
| 8,275,457 B1 | 9/2012 | Fischell et al. | |
| 8,301,236 B2 | 10/2012 | Baumann et al. | |
| 8,323,189 B2 * | 12/2012 | Tran ...................... A61B 5/1112 600/300 | |
| 8,332,233 B2 | 12/2012 | Ott et al. | |
| 8,352,018 B2 | 1/2013 | Xue | |
| 8,369,936 B2 | 2/2013 | Farringdon et al. | |
| 8,401,644 B2 | 3/2013 | Gunderson et al. | |
| 8,423,128 B2 | 4/2013 | Goto | |
| 8,433,399 B1 | 4/2013 | Nosrati et al. | |
| 8,437,840 B2 | 5/2013 | Patel et al. | |
| 8,461,988 B2 | 6/2013 | Tran | |
| 8,473,065 B2 | 6/2013 | Matos | |
| 8,483,807 B2 | 7/2013 | Kurzweil et al. | |
| 8,512,257 B2 | 8/2013 | Fischell et al. | |
| 8,521,281 B2 | 8/2013 | Patel et al. | |
| 8,525,673 B2 | 9/2013 | Tran | |
| 8,525,687 B2 | 9/2013 | Tran | |
| 8,531,291 B2 | 9/2013 | Tran | |
| 8,554,315 B2 | 10/2013 | Cho et al. | |
| 8,560,069 B2 | 10/2013 | Zhang | |
| 8,562,524 B2 | 10/2013 | Osorio | |
| 8,565,882 B2 | 10/2013 | Matos | |
| 8,583,251 B2 | 11/2013 | Matos | |
| 8,630,702 B2 | 1/2014 | Fischell et al. | |
| 8,680,991 B2 | 3/2014 | Tran | |
| 8,682,284 B2 | 3/2014 | Brackett et al. | |
| 8,684,922 B2 | 4/2014 | Tran | |
| 8,706,217 B2 | 4/2014 | Bardy et al. | |
| 8,706,225 B2 | 4/2014 | Matos | |
| 8,712,509 B2 * | 4/2014 | Lee ................... A61B 5/02405 607/30 | |
| 8,718,752 B2 | 5/2014 | Libbus et al. | |
| 8,738,120 B2 | 5/2014 | Björling et al. | |
| 8,747,336 B2 | 6/2014 | Tran | |
| 8,774,908 B2 | 7/2014 | Stewart | |
| 8,774,909 B2 | 7/2014 | Patel et al. | |
| 8,805,529 B2 | 8/2014 | Matos | |
| 8,825,146 B2 | 9/2014 | Li | |
| 8,831,725 B2 | 9/2014 | Gunderson et al. | |
| 8,849,400 B2 | 9/2014 | Gunderson et al. | |
| 8,855,550 B2 | 10/2014 | Gaines et al. | |
| 8,862,393 B2 | 10/2014 | Zhou et al. | |
| 8,886,296 B2 | 11/2014 | Patel | |
| 8,909,332 B2 | 12/2014 | Vitali et al. | |
| 8,923,960 B2 | 12/2014 | Goto | |
| 8,954,137 B2 | 2/2015 | Kurzweil et al. | |
| 8,965,494 B2 | 2/2015 | Fischell et al. | |
| 8,983,587 B2 | 3/2015 | Kurzweil et al. | |
| 8,983,682 B1 | 3/2015 | Peeters et al. | |
| 9,028,405 B2 | 5/2015 | Tran | |
| 9,031,645 B2 | 5/2015 | Houben et al. | |
| 9,044,148 B2 | 6/2015 | Michaelson et al. | |
| 9,060,746 B2 | 6/2015 | Weng et al. | |
| 9,082,156 B2 | 7/2015 | Matos | |
| 9,095,727 B2 | 8/2015 | Matos | |
| 9,101,278 B2 | 8/2015 | Fischell et al. | |
| 9,113,830 B2 | 8/2015 | Galen et al. | |
| 9,138,590 B2 | 9/2015 | Zhang et al. | |
| 9,179,255 B2 | 11/2015 | Stephens et al. | |
| 9,179,851 B2 | 11/2015 | Baumann et al. | |
| 9,204,796 B2 | 12/2015 | Tran | |
| 9,237,243 B2 | 1/2016 | Jensen et al. | |
| 9,241,677 B2 | 1/2016 | Liao-Chen et al. | |
| 9,254,092 B2 | 2/2016 | Albert et al. | |

(56)                 References Cited

U.S. PATENT DOCUMENTS

| 9,293,025 | B2 | 3/2016 | Zhang |
| 9,307,383 | B1 | 4/2016 | Patrick |
| 9,314,181 | B2 | 4/2016 | Brockway et al. |
| 9,351,640 | B2 | 5/2016 | Tran |
| 9,364,158 | B2 | 6/2016 | Banet et al. |
| 9,445,736 | B2 | 9/2016 | Kurzweil et al. |
| 9,456,787 | B2 | 10/2016 | Venkatraman et al. |
| 9,468,383 | B2 | 10/2016 | Fischell et al. |
| 9,491,277 | B2 | 11/2016 | Vincent |
| 9,498,152 | B2 | 11/2016 | Bowers |
| 9,642,167 | B1 | 5/2017 | Snyder et al. |
| 9,662,015 | B2 | 5/2017 | Proud et al. |
| 9,668,665 | B2 | 6/2017 | Schroeder et al. |
| 9,681,814 | B2 | 6/2017 | Galloway et al. |
| 9,724,008 | B2 | 8/2017 | Sullivan et al. |
| 9,724,046 | B2 | 8/2017 | Forstner |
| 9,730,604 | B2 | 8/2017 | Li et al. |
| 9,735,896 | B2 | 8/2017 | Flippo et al. |
| 9,770,181 | B2 | 9/2017 | Kurzweil et al. |
| 9,775,520 | B2 | 10/2017 | Tran |
| 9,820,667 | B2 | 11/2017 | Ting et al. |
| 9,824,188 | B2 | 11/2017 | Brown et al. |
| 9,826,358 | B2 | 11/2017 | Ryan et al. |
| 9,852,599 | B1 | 12/2017 | Slavin et al. |
| 9,855,434 | B2 | 1/2018 | Matos |
| 9,901,252 | B2 | 2/2018 | Tran |
| 9,913,583 | B2 | 3/2018 | Smith, Sr. |
| 9,979,810 | B2 | 5/2018 | Mazar et al. |
| 9,997,055 | B2 | 6/2018 | Ball |
| 10,003,394 | B2 | 6/2018 | Bromberg et al. |
| 10,039,469 | B2 | 8/2018 | Higgins et al. |
| 10,044,857 | B2 | 8/2018 | Philbin |
| 10,085,115 | B2 | 9/2018 | Mayor et al. |
| 10,098,561 | B2 | 10/2018 | Brockway et al. |
| 10,117,595 | B2 | 11/2018 | Chang et al. |
| 10,117,606 | B2 | 11/2018 | Feldman et al. |
| 10,123,741 | B2 | 11/2018 | Wang et al. |
| 10,136,826 | B2 | 11/2018 | Sullivan et al. |
| 10,165,400 | B2 | 12/2018 | Raj |
| 10,201,710 | B2 | 2/2019 | Jackson et al. |
| 10,206,593 | B2 | 2/2019 | Ukil et al. |
| 10,272,010 | B2 | 4/2019 | Freeman et al. |
| 10,278,050 | B2 | 4/2019 | Winkler et al. |
| 10,278,607 | B2 | 5/2019 | Prystowsky et al. |
| 10,307,060 | B2 | 6/2019 | Tran |
| 10,362,940 | B2 | 7/2019 | Tran |
| 10,368,807 | B2 | 8/2019 | Melker et al. |
| 10,375,558 | B2 | 8/2019 | Katz et al. |
| 10,420,529 | B2 | 9/2019 | Wang et al. |
| 10,463,295 | B2 | 11/2019 | Zhou |
| 10,492,686 | B2 | 12/2019 | Hunter et al. |
| 10,493,290 | B2 | 12/2019 | Ludwig et al. |
| 10,517,479 | B2 | 12/2019 | Tran |
| 10,524,736 | B2 | 1/2020 | Gross |
| 10,531,266 | B2 | 1/2020 | Rauner et al. |
| 10,537,263 | B2 | 1/2020 | Ibáñez Català |
| 10,540,878 | B2 | 1/2020 | Hunter et al. |
| 10,575,748 | B2 | 3/2020 | Higgins et al. |
| 10,595,731 | B2 | 3/2020 | Gopalakrishnan et al. |
| 10,602,942 | B2 | 3/2020 | Shakur et al. |
| 10,616,664 | B2 | 4/2020 | Alman et al. |
| 10,616,747 | B2 | 4/2020 | Piett et al. |
| 10,617,356 | B2 | 4/2020 | Wang et al. |
| 10,624,550 | B2 | 4/2020 | Soli et al. |
| 10,631,742 | B2 | 4/2020 | Tal et al. |
| 10,631,744 | B2 * | 4/2020 | Mahajan ............ A61N 1/36592 |
| 10,657,796 | B2 | 5/2020 | Bowers |
| 10,674,342 | B2 | 6/2020 | Park et al. |
| 10,702,213 | B2 | 7/2020 | Sharma et al. |
| 10,736,532 | B2 | 8/2020 | Bardy et al. |
| 10,758,140 | B2 | 9/2020 | Kurzweil et al. |
| 10,796,552 | B2 | 10/2020 | Fahey |
| 10,814,978 | B2 | 10/2020 | Walker et al. |
| 10,882,180 | B2 | 1/2021 | Wright et al. |
| 10,888,705 | B2 | 1/2021 | Matos |
| 10,905,328 | B2 | 2/2021 | Murphy et al. |
| 10,981,009 | B2 | 4/2021 | Jackson et al. |
| 11,024,432 | B2 | 6/2021 | Chiu et al. |
| 11,064,339 | B2 | 7/2021 | Hamre et al. |
| 11,103,176 | B2 | 8/2021 | Galloway et al. |
| 11,103,194 | B2 | 8/2021 | Galloway et al. |
| 11,116,448 | B1 | 9/2021 | Trapero Martin et al. |
| 11,116,989 | B2 | 9/2021 | Gill et al. |
| 11,160,484 | B2 | 11/2021 | Sullivan et al. |
| 11,197,629 | B2 | 12/2021 | Remes et al. |
| 11,198,017 | B2 | 12/2021 | Kaib et al. |
| 11,202,174 | B2 | 12/2021 | Klinkner et al. |
| 11,218,584 | B2 | 1/2022 | Martin et al. |
| 11,219,373 | B2 | 1/2022 | Eggers et al. |
| 11,228,891 | B2 | 1/2022 | King-Berkman et al. |
| 11,230,242 | B2 | 1/2022 | Makled et al. |
| 11,234,604 | B2 | 2/2022 | Albert |
| 11,278,201 | B2 | 3/2022 | Thomson et al. |
| 11,289,197 | B1 | 3/2022 | Park et al. |
| 11,291,401 | B2 | 4/2022 | Velo |
| 11,311,230 | B2 | 4/2022 | Sullivan et al. |
| 11,331,475 | B2 | 5/2022 | Drake et al. |
| 11,341,839 | B2 | 5/2022 | Cruver et al. |
| 11,344,244 | B2 | 5/2022 | Albert |
| 11,363,952 | B2 | 6/2022 | Venkatraman et al. |
| 11,406,314 | B2 | 8/2022 | Henry et al. |
| 11,623,102 | B2 | 4/2023 | Schulhauser et al. |
| 11,633,112 | B2 | 4/2023 | Stadler et al. |
| 11,679,268 | B2 | 6/2023 | Haddad et al. |
| 11,684,776 | B2 | 6/2023 | Grubac et al. |
| 12,142,351 | B2 | 11/2024 | Pinter et al. |
| 2002/0032383 | A1 | 3/2002 | Weil et al. |
| 2003/0023175 | A1 | 1/2003 | Arzbaecher et al. |
| 2003/0176798 | A1 | 9/2003 | Simon |
| 2003/0191402 | A1 | 10/2003 | Arzbaecher et al. |
| 2003/0214409 | A1 | 11/2003 | Hickle |
| 2003/0233129 | A1 | 12/2003 | Matos |
| 2004/0172069 | A1 | 9/2004 | Hakala |
| 2004/0199212 | A1 * | 10/2004 | Fischell ............. A61N 1/37258 607/32 |
| 2005/0065445 | A1 | 3/2005 | Arzbaecher et al. |
| 2005/0154325 | A1 | 7/2005 | Lauter et al. |
| 2005/0228305 | A1 | 10/2005 | Nagata et al. |
| 2005/0234313 | A1 | 10/2005 | Rowlandson et al. |
| 2006/0030781 | A1 | 2/2006 | Shennib |
| 2006/0155206 | A1 | 7/2006 | Lynn |
| 2006/0173498 | A1 | 8/2006 | Banville et al. |
| 2006/0264767 | A1 | 11/2006 | Shennib |
| 2006/0284732 | A1 | 12/2006 | Brock-Fisher |
| 2007/0043585 | A1 | 2/2007 | Matos |
| 2007/0049976 | A1 | 3/2007 | Ni et al. |
| 2007/0249944 | A1 | 10/2007 | Fischell et al. |
| 2007/0260285 | A1 | 11/2007 | Libbus et al. |
| 2007/0260289 | A1 | 11/2007 | Giftakis et al. |
| 2007/0293775 | A1 | 12/2007 | Fischell et al. |
| 2007/0299473 | A1 | 12/2007 | Matos |
| 2008/0058660 | A1 | 3/2008 | Fischell et al. |
| 2008/0064973 | A1 | 3/2008 | Fischell et al. |
| 2008/0139954 | A1 | 6/2008 | Day et al. |
| 2008/0177194 | A1 | 7/2008 | Zhang et al. |
| 2008/0270036 | A1 | 10/2008 | Webb |
| 2009/0054027 | A1 | 2/2009 | Jenkins |
| 2009/0062670 | A1 | 3/2009 | Sterling et al. |
| 2009/0076559 | A1 | 3/2009 | Libbus et al. |
| 2009/0149849 | A1 | 6/2009 | Lin et al. |
| 2009/0240156 | A1 | 9/2009 | Fischell et al. |
| 2009/0322513 | A1 | 12/2009 | Hwang et al. |
| 2009/0326595 | A1 | 12/2009 | Brockway et al. |
| 2010/0016746 | A1 | 1/2010 | Hampton et al. |
| 2010/0022902 | A1 | 1/2010 | Lee et al. |
| 2010/0286490 | A1 | 11/2010 | Koverzin et al. |
| 2011/0054934 | A1 | 3/2011 | Vesto |
| 2011/0105928 | A1 | 5/2011 | Bojovic et al. |
| 2011/0112417 | A1 | 5/2011 | Gunderson et al. |
| 2011/0193704 | A1 | 8/2011 | Harper et al. |
| 2011/0230161 | A1 | 9/2011 | Newman |
| 2011/0288417 | A1 * | 11/2011 | Pinter .................... G16Z 99/00 600/595 |
| 2012/0190969 | A1 | 7/2012 | Kameli |

(56)     References Cited

U.S. PATENT DOCUMENTS

| | | | |
|---|---|---|---|
| 2012/0191150 A1 | 7/2012 | Kameli | |
| 2012/0191151 A1 | 7/2012 | Kameli | |
| 2012/0191152 A1 | 7/2012 | Kameli | |
| 2012/0220835 A1 | 8/2012 | Chung | |
| 2012/0242501 A1* | 9/2012 | Tran | A61B 5/0024 |
| | | | 340/870.02 |
| 2012/0306652 A1 | 12/2012 | Musol et al. | |
| 2012/0330171 A1 | 12/2012 | Zhang et al. | |
| 2013/0095459 A1 | 4/2013 | Tran | |
| 2013/0211291 A1 | 8/2013 | Tran | |
| 2013/0245466 A1 | 9/2013 | Sachanandani et al. | |
| 2014/0100497 A1 | 4/2014 | Hayashi et al. | |
| 2014/0152436 A1 | 6/2014 | Langer | |
| 2014/0163425 A1 | 6/2014 | Tran | |
| 2014/0213202 A1 | 7/2014 | Wang et al. | |
| 2014/0293053 A1 | 10/2014 | Chuang | |
| 2015/0018658 A1 | 1/2015 | Fischell et al. | |
| 2015/0045868 A1 | 2/2015 | Bonner et al. | |
| 2015/0105632 A1 | 4/2015 | Melker et al. | |
| 2015/0112605 A1 | 4/2015 | Watson et al. | |
| 2015/0118658 A1 | 4/2015 | Mayou et al. | |
| 2015/0158988 A1 | 6/2015 | Sawaki et al. | |
| 2015/0164375 A1 | 6/2015 | Schindhelm et al. | |
| 2015/0173689 A1 | 6/2015 | Owen et al. | |
| 2015/0223759 A1 | 8/2015 | Ong et al. | |
| 2015/0302539 A1 | 10/2015 | Mazar et al. | |
| 2015/0366518 A1 | 12/2015 | Sampson | |
| 2016/0000349 A1 | 1/2016 | Sullivan et al. | |
| 2016/0008614 A1 | 1/2016 | Zhang et al. | |
| 2016/0035204 A1 | 2/2016 | Jansen | |
| 2016/0106378 A1 | 4/2016 | Kyal et al. | |
| 2016/0120434 A1 | 5/2016 | Park et al. | |
| 2016/0128595 A1 | 5/2016 | Fischell et al. | |
| 2016/0135706 A1* | 5/2016 | Sullivan | A61B 5/7275 |
| | | | 600/509 |
| 2016/0151021 A1 | 6/2016 | Feng et al. | |
| 2016/0174857 A1 | 6/2016 | Eggers et al. | |
| 2016/0174875 A1 | 6/2016 | Forster et al. | |
| 2016/0325107 A1 | 11/2016 | Park et al. | |
| 2016/0328950 A1 | 11/2016 | Pelletier et al. | |
| 2016/0331330 A1 | 11/2016 | Freeman et al. | |
| 2016/0354011 A1 | 12/2016 | Stahl | |
| 2017/0007167 A1 | 1/2017 | Kostic et al. | |
| 2017/0083667 A1 | 3/2017 | Darrah et al. | |
| 2017/0099579 A1 | 4/2017 | Ryan et al. | |
| 2017/0246329 A1 | 8/2017 | Lloyd | |
| 2017/0281097 A1 | 10/2017 | Thakur et al. | |
| 2017/0296076 A1* | 10/2017 | Mahajan | A61N 1/37 |
| 2017/0323485 A1 | 11/2017 | Samec et al. | |
| 2017/0330438 A1 | 11/2017 | Howard et al. | |
| 2017/0354365 A1 | 12/2017 | Zhou | |
| 2017/0360361 A1 | 12/2017 | Long et al. | |
| 2017/0366921 A1 | 12/2017 | Pflugh et al. | |
| 2018/0008159 A1 | 1/2018 | Wang et al. | |
| 2018/0091657 A1 | 3/2018 | Brown et al. | |
| 2018/0113986 A1 | 4/2018 | Zhu | |
| 2018/0113987 A1 | 4/2018 | Zhu | |
| 2018/0116537 A1 | 5/2018 | Sullivan et al. | |
| 2018/0117299 A1 | 5/2018 | Gustavson et al. | |
| 2018/0146922 A1 | 5/2018 | Wang et al. | |
| 2018/0192894 A1 | 7/2018 | An et al. | |
| 2018/0220897 A1 | 8/2018 | Meger et al. | |
| 2018/0221645 A1 | 8/2018 | Medema et al. | |
| 2018/0235537 A1 | 8/2018 | Whiting et al. | |
| 2018/0243578 A1 | 8/2018 | Volosin | |
| 2018/0260706 A1 | 9/2018 | Galloway et al. | |
| 2018/0301017 A1 | 10/2018 | Dizengof et al. | |
| 2018/0322405 A1 | 11/2018 | Fadell et al. | |
| 2018/0338731 A1 | 11/2018 | Addison et al. | |
| 2018/0348759 A1 | 12/2018 | Freeman et al. | |
| 2019/0043616 A1 | 2/2019 | Howard et al. | |
| 2019/0066538 A1 | 2/2019 | Chao et al. | |
| 2019/0083804 A1 | 3/2019 | Grinberg et al. | |
| 2019/0125273 A1 | 5/2019 | Sharma et al. | |
| 2019/0197861 A1 | 6/2019 | Tunnell et al. | |

| | | |
|---|---|---|
| 2019/0275225 A1 | 9/2019 | Brown |
| 2019/0279480 A1 | 9/2019 | Lee et al. |
| 2019/0290216 A1 | 9/2019 | Koyama |
| 2019/0298201 A1 | 10/2019 | Persen et al. |
| 2019/0307328 A1 | 10/2019 | Tran |
| 2019/0328251 A1 | 10/2019 | Jin |
| 2019/0336767 A1 | 11/2019 | Klepfer et al. |
| 2019/0365264 A1 | 12/2019 | Freeman et al. |
| 2019/0365269 A1 | 12/2019 | Jun |
| 2019/0391581 A1 | 12/2019 | Vardaro et al. |
| 2020/0008696 A1 | 1/2020 | Sirendi et al. |
| 2020/0038671 A1 | 2/2020 | Schulhauser et al. |
| 2020/0046241 A1 | 2/2020 | Lam et al. |
| 2020/0069245 A1 | 3/2020 | Zhou |
| 2020/0077892 A1 | 3/2020 | Tran |
| 2020/0085380 A1 | 3/2020 | Sampson |
| 2020/0100693 A1 | 4/2020 | Velo |
| 2020/0113459 A1 | 4/2020 | Jäntti et al. |
| 2020/0146550 A1 | 5/2020 | Tunnell et al. |
| 2020/0160991 A1 | 5/2020 | Smith et al. |
| 2020/0178821 A1 | 6/2020 | Wu et al. |
| 2020/0305737 A1 | 10/2020 | Tseng et al. |
| 2020/0337567 A1 | 10/2020 | McCalmont et al. |
| 2020/0337581 A1 | 10/2020 | Jung et al. |
| 2020/0342966 A1 | 10/2020 | Stern et al. |
| 2020/0352462 A1 | 11/2020 | Pedalty et al. |
| 2020/0352466 A1 | 11/2020 | Chakravarthy et al. |
| 2020/0352522 A1 | 11/2020 | Chakravarthy et al. |
| 2020/0357519 A1 | 11/2020 | Chakravarthy et al. |
| 2020/0373005 A1 | 11/2020 | Halsne et al. |
| 2020/0380840 A1 | 12/2020 | Galarneau et al. |
| 2020/0390354 A1 | 12/2020 | Huegerich et al. |
| 2020/0397308 A1 | 12/2020 | Sarkar et al. |
| 2021/0118562 A1 | 4/2021 | Matos |
| 2021/0121090 A1 | 4/2021 | Weinstein et al. |
| 2021/0138243 A1 | 5/2021 | Zhang et al. |
| 2021/0138254 A1 | 5/2021 | Matos |
| 2021/0154487 A1 | 5/2021 | Bongberg et al. |
| 2021/0169392 A1 | 6/2021 | Albert et al. |
| 2021/0186329 A1 | 6/2021 | Tran |
| 2021/0251578 A1 | 8/2021 | Schulhauser et al. |
| 2021/0259560 A1 | 8/2021 | Venkatraman et al. |
| 2021/0314756 A1 | 10/2021 | Brooks et al. |
| 2021/0338134 A1 | 11/2021 | Chakravarthy et al. |
| 2021/0338138 A1 | 11/2021 | Pedalty et al. |
| 2021/0343132 A1 | 11/2021 | Bonser |
| 2021/0343416 A1 | 11/2021 | Chakravarthy et al. |
| 2021/0345934 A1 | 11/2021 | Landgraf et al. |
| 2021/0353166 A1 | 11/2021 | Sirendi et al. |
| 2021/0401349 A1 | 12/2021 | Schram |
| 2022/0023626 A1 | 1/2022 | Haddad et al. |
| 2022/0031253 A1 | 2/2022 | Burnes et al. |
| 2022/0039729 A1 | 2/2022 | Fontanarava et al. |
| 2022/0051548 A1 | 2/2022 | Pellegrini et al. |
| 2022/0061678 A1 | 3/2022 | Schulhauser et al. |
| 2022/0095982 A1 | 3/2022 | de Saint Victor et al. |
| 2022/0151533 A1 | 5/2022 | Moon |
| 2022/0160250 A1 | 5/2022 | Anderson et al. |
| 2022/0183607 A1 | 6/2022 | Volosin et al. |
| 2022/0218259 A1 | 7/2022 | Laversin et al. |
| 2022/0249026 A1 | 8/2022 | Heneghan et al. |
| 2022/0280047 A1 | 9/2022 | Stadler et al. |
| 2022/0346725 A1 | 11/2022 | Krause et al. |
| 2022/0369937 A1 | 11/2022 | Cho et al. |
| 2023/0263406 A1 | 8/2023 | Stadler et al. |

FOREIGN PATENT DOCUMENTS

| | | |
|---|---|---|
| CN | 105769171 A | 7/2016 |
| CN | 106264518 A | 1/2017 |
| CN | 106562777 A | 4/2017 |
| CN | 107874753 A | 4/2018 |
| CN | 108039203 A | 5/2018 |
| CN | 108324264 A | 7/2018 |
| CN | 207924885 U | 9/2018 |
| CN | 109009047 A | 12/2018 |
| CN | 208460154 U | 2/2019 |
| CN | 109820492 A | 5/2019 |
| CN | 109953753 A | 7/2019 |

(56) References Cited

FOREIGN PATENT DOCUMENTS

| CN | 111667921 A | 9/2020 |
|---|---|---|
| CN | 112022145 A | 12/2020 |
| CN | 112515650 A | 3/2021 |
| CN | 112515651 A | 3/2021 |
| CN | 113080917 A | 7/2021 |
| CN | 113598784 A | 11/2021 |
| CN | 215128553 U | 12/2021 |
| CN | 114711781 A | 7/2022 |
| CN | 217014071 U | 7/2022 |
| EP | 2689363 A2 | 1/2014 |
| ES | 2559263 T3 | 2/2016 |
| FI | 128143 B | 12/2018 |
| GB | 2569157 A | 6/2019 |
| GB | 2590556 B | 6/2021 |
| GB | 2600710 A | 5/2022 |
| IN | 201811048444 A | 12/2018 |
| JP | 3031277 B2 | 4/2000 |
| JP | 2007289694 A | 11/2007 |
| JP | 2009089883 A | 4/2009 |
| JP | 6764830 A | 12/2018 |
| JP | 2019129954 A | 8/2019 |
| KR | 20030008655 A | 1/2003 |
| KR | 100400212 B1 | 11/2003 |
| KR | 100637566 B1 | 10/2006 |
| KR | 101756787 B1 | 7/2017 |
| KR | 102195189 B1 | 12/2020 |
| MX | 2016007079 A | 11/2017 |
| SU | 442789 A1 | 9/1974 |
| SU | 1042732 A1 | 9/1983 |
| TR | 201719097 A2 | 6/2019 |
| TW | M555707 U | 2/2018 |
| TW | I669097 B | 8/2019 |
| WO | 2005021089 A1 | 3/2005 |
| WO | 2009001361 A2 | 12/2008 |
| WO | 2010105053 A3 | 1/2011 |
| WO | 2012135059 A2 | 10/2012 |
| WO | 2016034203 A1 | 3/2016 |
| WO | 2017059274 A1 | 4/2017 |
| WO | 2018202606 A1 | 11/2018 |
| WO | 2019096876 A1 | 5/2019 |
| WO | 2019110963 A1 | 6/2019 |
| WO | 2020115747 A1 | 6/2020 |
| WO | 2020155078 A1 | 8/2020 |
| WO | 2020226879 | 11/2020 |
| WO | 2020226881 | 11/2020 |
| WO | 2020226887 | 11/2020 |
| WO | 2021084535 | 5/2021 |
| WO | 2021133360 A1 | 7/2021 |
| WO | 2021181389 A1 | 9/2021 |
| WO | 2022034045 | 2/2022 |
| WO | 2022034480 | 2/2022 |
| WO | 2022070109 | 4/2022 |
| WO | 2022130152 | 6/2022 |

OTHER PUBLICATIONS

"Heart Disease and Stroke Statistics—2019 Update a Report From the American Heart Association," Circulation, vol. 139, Mar. 5, 2019 pp. e56-e528.

"Highlights of the 2020 American Heart Association Guidelines for CPR and ECC," American Heart Association, 2020 (Applicant points out, in accordance with MPEP 609.04(a), that the year of publication, 2020, is sufficiently earlier than the effective U.S. filing date, so that the particular month of publication is not in issue.) 32 p.

"Monitor your heart rate with Apple Watch," retrieved from https://support.apple.com/en-us/HT204666, on Apr. 23, 2021, 8 pp.

"Protocol 9, Cardiac or Respiratory Arrest," The EMD Protocol, National Academy Medical Prioity Dispatch System, Accessed on Apr. 23, 2021, 5 pp.

"Using Apple Watch for Arrhythmia Detection," Apple, Inc., Dec. 2020, 17 pp.

Auer et al., "A Smartwatch to Identify Atrial Fibrillation," The New England Journal of Medicine, vol. 382, No. 10, Mar. 5, 2020, pp. 974-976.

Bayanbay et al., "The Use of Unmanned Aerial Vehicle for Emergency Medical Assistance," 2019 20th International Conference of Young Specialists on Micro/Nanotechnologies and Electron Devices (EDM), Jun. 29-Jul. 3, 2019, pp. 597-600.

Beauchamp et al., "The Use of Wearables in Clinical Trials During Cancer Treatment: Systematic Review," JMIR Mhealth Uhealth, vol. 8, No. 11, e22006, Nov. 2020, 15 pp.

Blomberg et al., "Effect of Machine Learning on Dispatcher Recognition of Out-of-Hospital Cardiac Arrest During Calls to Emergency Medical Services a Randomized Clinical Trial," JAMA Network Open, Jan. 6, 2021, 10 pp.

Book of Abstracts, Acta Cardiologica, vol. 76, supp 1, Feb. 22, 2021, 52 pp.

Bumgarner et al., "Smartwatch Algorithm for Automated Detection of Atrial Fibrillation," Journal of the American College of Cardiology, vol. 71, No. 21, May 29, 2018, pp. 2381-2388.

Burke et al., "Smartwatch Detection of Ventricular Tachycardia: Case Series," Heart Rhythm Case Reports, vol. 6, No. 10, Oct. 2020, pp. 801-804.

Campion et al., "Watched by Apple," The New England Journal of Medicine, vol. 381, No. 20, Nov. 14, 2019, pp. 1964-1965.

CARES Annual Report 2019, 2019 (Applicant points out, in accordance with MPEP 609.04(a), that the year of publication, 2019, is sufficiently earlier than the effective U.S. filing date, so that the particular month of publication is not in issue.) 48 pp.

Carpenter et al., "Smart-Watches: a Potential Challenger to the Implantable Loop Recorder?," Europace, vol. 18, Feb. 2016, pp. 791-793.

Centers for Disease Control and Prevention et al., "What is v-safe?", Jun. 10, 2022, 1 pp., URL: https://www.cdc.gov/coronavirus/2019-ncov/vaccines/safety/pdfs/v-safe-information-sheet-508c.pdf.

Chan et al., "Contactless Cardiac Arrest Detection Using Smart Devices," NPJ Digital Medicine, vol. 2, No. 52, Jun. 19, 2019, 8 pp.

Dayananda et al., "An Interconnected Architecture for an Emergency Medical Response Unmanned Aerial System," 2017 IEEE/AIAA 36th Digital Avionics Systems Conference (DASC), Sep. 17-21, 2017, pp. 1-6.

Deo et al., "Epidemiology and Genetics of Sudden Cardiac Death," Circulation, vol. 125, No. 4, Jan. 31, 2012, pp. 620-637.

Giancaterino et al., "The Smartwatch Will See You Now: Implications of Mass Screening for Atrial Fibrillation," Journal of the American College of Cardiology, vol. 72, No. 12, Sep. 18, 2018, pp. 1433-1434.

Goldberger et al., "Risk Stratification for Sudden Cardiac Death a Plan for the Future," Circulation, vol. 129, No. 4, Jan. 28, 2014, pp. 516-526.

Hause et al., "COVID-19 Vaccine Safety in Adolescents Aged 12-17 Years—United States, Dec. 14, 2020-Jul. 16, 2021", Centers for Disease Control and Prevention, Jul. 30, 2021, 9 pp., URL: https://www.cdc.gov/mmwr/volumes/70/wr/mm7031e1.htm.

Hirano et al., "Early Outcome Prediction for Out-of-Hospital Cardiac Arrest with Initial Shockable Rhythm Using Machine Learning Models," Resuscitation, vol. 158, No. 145, Jan. 2021, pp. 49-56.

Hwang et al., "Assessing Accuracy of Wrist-Worn Wearable Devices in Measurement of Paroxysmal Supraventricular Tachycardia Heart Rate," Korean Circulation Journal, vol. 49, No. 5, May 2019, pp. 437-445.

Instructions for Irregular Rhythm Notification, Apple Inc., Jun. 2020, 154 pp.

International Preliminary Report on Patentability from International Application No. PCT/US2022/070616 dated Sep. 21, 2001, 8 pp.

International Search Report and Written Opinion of International Application No. PCT/US2022/070616, dated May 17, 2022, 11 pp.

Koshy et al., "Smart Watches for Heart Rate Assessment in Atrial Arrhythmias," International Journal of Cardiology, vol. 266, Sep. 1, 2018, pp. 124-127.

Li et al., "The Current State of Mobile Phone Apps for Monitoring Heart Rate, Heart Rate Variability, and Atrial Fibrillation: Narrative Review," JMIR Mhealth Uhealth, vol. 7, No. 2, e11606, Feb. 15, 2019, 16 pp.

(56)          References Cited

OTHER PUBLICATIONS

Medtronic Linq II, Medtronic CareLink Network, Jan. 29, 2021, 11 pp.

Mell et al., "Emergency Medical Services Response Times in Rural, Suburban, and Urban Areas," JAMA Surgery, vol. 152, No. 10, Oct. 2017, pp. 983-984.

Okubo et al., "Characteristics of Paediatric Out-of-Hospital Cardiac Arrest in the United States," Resuscitation, vol. 153, Apr. 27, 2020, pp. 227-233.

Papini et al., "Wearable Monitoring of Sleep-Disordered Breathing: Estimation of the Apnea-Hypopnea Index Using Wrist-Worn Reflective Photoplethysmography," Scientific Reports, vol. 10, No. 13512, Aug. 11, 2020, 15 pp.

Perez et al., "Large-Scale Assessment of a Smartwatch to Identify Atrial Fibrillation," The New England Journal of Medicine, vol. 381, No. 20, Nov. 14, 2019, pp. 1909-1917.

Pulsepoint, "Activate Citizen Response.", Building informed communities, 14 pp., Retrieved from the Internet on Oct. 25, 2021 from URL: ttps://www.pulsepoint.org.

Ringwald et al., "Smart Watch Recording of Ventricular Tachycardia: Case Study," American Journal of Emergency Medicine, vol. 38, No. 4, Apr. 1, 2020, pp. 849.e3-849.e5.

Roberts et al., "Best Buy makes deal to provide its senior services on Apple Watch", Star Tribune, Mar. 3, 2021, 2 pp., URL: https://www.startribune.com/best-buy-makes-deal-to-provide-its-senior-services-on-apple-watch/600029754/.

Rudner et al., "Interrogation of Patient Smartphone Activity Tracker to Assist Arrhythmia Management," Annals of Emergency Medicine, vol. 68, No. 3, Sep. 2016, pp. 292-294.

Salcido et al., "Have Outcomes After Out of Hospital Cardiac Arrest Improved Over Time?," Circulation: Cardiovascular Quality and Outcomes, vol. 14, No. 3, e007752, Mar. 2021, pp. 290-291.

Samani et al., "Robotic Automated External Defibrillator Ambulance for Emergency Medical Service in Smart Cities", vol. 4, IEEE, Jan. 4, 2016, pp. 268-283.

Samsung Galaxy Watch3 LTE Smartwatch, retrieved from https://www.samsung.com/us/watches/galaxywatch3/# health, on Apr. 29, 2021, 31 pp.

Seifert, "Say hello to Astro, Alexa on wheels", The Verge, Sep. 28, 2021, 18 pp., URL: https://www.theverge.com/2021/9/28/22697244/amazon-astro-home-robot-hands-on-features-price.

Seshadri et al., "Accuracy of Apple Watch for Detection of Atrial Fibrillation," Circulation, vol. 141, No. 8, Feb. 25, 2020, pp. 702-703.

Shcherbina et al., "Accuracy in Wrist-Worn, Sensor-Based Measurements of Heart Rate and Energy Expenditure in a Diverse Cohort," Journal of Personalized Medicine, vol. 3, No. 7, May 24, 2017, 12 pp.

Singh, "Detecting Atrial Fibrillation with with the Apple Watch: Our Clinically Validated Results," https://blog.cardiogr.am/detecting-atrial-fibrillation-with-the-apple-watch-our-clinically-validated-resultsea66163e0fa6, Mar. 21, 2018, 14 pp.

Singhal et al., "The Role of Wearables in Heart Failure," Current Heart Failure Reports, vol. 17, No. 4, Jun. 3, 2020, pp. 125-132.

Solomon et al., "Sudden Death in Patients with Myocardial Infarction and Left Ventricular Dysfunction, Heart Failure, or Both," vol. 352, No. 25, Jun. 23, 2005, pp. 2581-2588.

Sudden Cardiac Arrest Meeting the Challenge, The Joint Commission, 2011 (Applicant points out, in accordance with MPEP 609.

04(a), that the year of publication, 2011, is sufficiently earlier than the effective U.S. filing date, so that the particular month of publication is not in issue.) 87 pp.

Tarakji et al., "Using a Novel Wireless System for Monitoring Patients After the Atrial Fibrillation Ablation Procedure: The iTransmit Study," Heart Rhythm Journal, vol. 12, No. 3, Mar. 1, 2015, pp. 554-559.

Than et al., "Machine Learning to Predict the Likelihood of Acute Myocardial Infarction," Circulation, vol. 140, Sep. 10, 2019, pp. 899-909.

Tuohy, "Amazon is now accepting your applications for its home surveillance drone", The Verge, Sep. 29, 2021, 9 pp., URL: https://www.theverge.com/2021/9/28/22692048/ring-always-home-cam-drone-amazon-price-release-date-specs.

Turakhia et al., "Rationale and Design of a Large-Scale, App-Based Study to Identify Cardiac Arrhythmias Using a Smartwatch: The Apple Heart Study," American Heart Journal, vol. 207, Jan. 2019, pp. 66-75.

U.S. Appl. No. 16/593,739, filed Oct. 4, 2019, by Haddad et al.

U.S. Appl. No. 17/006,444, filed Aug. 28, 2020, by Schulhauser

U.S. Appl. No. 17/101,945, filed Nov. 23, 2020, by Anderson et al.

U.S. Appl. No. 17/301,923, filed Apr. 19, 2021, by Anderson et al.

U.S. Appl. No. 17/383,170, filed Jul. 22, 2021, naming inventors Haddad et al.

U.S. Appl. No. 17/459,713, filed Aug. 27, 2021, naming inventors Schulhauser et al.

U.S. Appl. No. 18/547,105, filed Feb. 16, 2022, naming inventors Stadler et al.

U.S. Appl. No. 18/549,227, filed Feb. 17, 2022, naming inventors Ousdigian et al.

U.S. Appl. No. 18/551,322, filed Feb. 17, naming inventors Neitzell et al.

U.S. Appl. No. 18/552,324, filed Feb. 17, 2022, naming inventors Sarkar et al.

U.S. Appl. No. 63/158,189, by Medtronic, Inc., filed Mar. 8, 2021.

U.S. Appl. No. 63/071,997, filed Aug. 28, 2020, naming inventors Schulhauser et al.

U.S. Appl. No. 63/158,189, filed Mar. 8, 2021, naming inventors Stadler et al.

U.S. Appl. No. 63/219,595, filed Jul. 8, 2021, naming inventors Gunderson et al.

U.S. Appl. No. 63/362,451, filed Apr. 4, 2022, naming inventors Galarneau et al.

Volosin et al., "Tachycardia detection performance of implantable loop recorders: results from a large 'real-life' patient cohort and patients with induced ventricular arrhythmias", Europace, vol. 15, No. 8, European Society of Cardiology, Aug. 1, 2013, pp. 1215-1222, URL: https://academic.oup.com/europace/article/15/8/1215/2398708.

Waldmann et al., "Temporal Trends of Out-of-Hospital Cardiac Arrests Without Resuscitation Attempt by Emergency Medical Services," Circulation: Cardiovascular Quality and Outcomes, vol. 14, No. e006626, Mar. 2021, pp. 279-289.

Wang et al., "Accuracy of Wrist-Worn Heart Rate Monitors," JAMA Cardiology, vol. 2, No. 1, Jan. 2017, pp. 104-106.

Wikipedia, "PulsePoint", Oct. 1, 2021, 12 pp., URL: https://en.wikipedia.org/wiki/PulsePoint.

Zaman et al., "Sudden Cardiac Death Early After Myocardial Infarction Pathogenesis, Risk Stratification, and Primary Prevention," Circulation, vol. 129, No. 23, Jun. 10, 2014, pp. 2426-2435.

* cited by examiner

RECEIVE A COMMUNICATION INDICATIVE OF AN ACUTE HEALTH EVENT OF A PATIENT — 300

IN RESPONSE TO THE COMMUNICATION, VERIFY THE ACUTE HEALTH EVENT — 302

BASED ON THE VERIFICATION OF THE ACUTE HEALTH EVENT, SEND AN ALERT REGARDING THE ACUTE HEALTH EVENT — 304

RECEIVE DATA SOURCE INFORMATION FOR PATIENT ⟋400

RECEIVE CONSENT INFORMATION FOR PATIENT ⟋402

DETERMINE CLINICAL DATA COLLECTION SCHEDULE FOR PATIENT ⟋404

COLLECT CLINICAL DATA OF PATIENT ACCORDING TO SCHEDULE ⟋406

ACUTE HEALTH EVENT MONITORING AND VERIFICATION

This application is a U.S. National Stage entry under 35 U.S.C. § 371 of International Application No. PCT/US2022/070616, filed Feb. 10, 2022, which claims priority from and the benefit of U.S. Provisional Patent Application Ser. No. 63/182,456, filed Apr. 30, 2021, and U.S. Provisional Patent Application Ser. No. 63/158,189, filed Mar. 8, 2021, the entire conent of each of which is incorporated herein by reference.

FIELD

This disclosure generally relates to systems including medical devices and, more particularly, to monitoring of patient health using such systems.

BACKGROUND

A variety of devices are configured to configured to monitor physiological signals of a patient. Such devices include implantable or wearable medical devices, as well as a variety of wearable health or fitness tracking devices. The physiological signals sensed by such devices include as examples, electrocardiogram (ECG) signals, respiration signals, perfusion signals, activity and/or posture signals, pressure signals, blood oxygen saturation signals, body composition, and blood glucose or other blood constituent signals. In general, using these signals, such devices facilitate monitoring and evaluating patient health over a number of months or years, outside of a clinic setting.

In some cases, such devices are configured to detect acute health events based on the physiological signals, such as episodes of cardiac arrhythmia, myocardial infarction, stroke, or seizure or other epileptic event. Example arrhythmia types include cardiac arrest (e.g., asystole), ventricular tachycardia (VT), and ventricular fibrillation (VF). The devices may store ECG and other physiological signal data collected during a time period including an episode as episode data. Such acute health events are associated with significant rates of death, particularly if not treated quickly.

For example, VF and other malignant tachyarrhythmias are the most commonly identified arrhythmia in sudden cardiac arrest (SCA) patients. If this arrhythmia continues for more than a few seconds, it may result in cardiogenic shock and cessation of effective blood circulation. The survival rate from SCA decreases between 7 and 10 percent for every minute that the patient waits for defibrillation. Consequently, sudden cardiac death (SCD) may result in a matter of minutes.

SUMMARY

In general, the disclosure describes techniques for verifying the occurrence of an acute health event in a patient. For example, sensing circuitry of an implantable medical device (IMD) may sense an indication that an acute health event is occurring in the patient. The IMD may communicatively connect to a verification device or system, such as a smartphone, wearable device, smart speaker, video camera, infrared camera, thermal camera, radar system, sonar system, lidar system, bed sensor, drone, robot, hearing aid(s) or other Internet of Things (IoT) device. The verification device or system may verify the acute health event and send an alert regarding the acute health event.

In one example, a device includes communication circuitry configured to receive a communication indicative of an acute health event of a patient, memory communicatively coupled to the communication circuitry and being configured to store the indication of the acute health event, and processing circuitry communicatively coupled to the communication circuitry and the memory, the processing circuitry being configured to: in response to the communication, verify the acute health event; and based on the verification of the acute health event, send an alert regarding the acute health event.

In another example, a method includes receiving, by a verification device, a communication indicative of an acute health event of a patient; in response to the communication, verifying, by the verification device, the acute health event; and based on the verification of the acute health event, sending an alert regarding the acute health event.

In another example, a non-transitory computer-readable storage medium stores instructions that, when executed, cause processing circuitry to in response to receiving a communication indicative of an acute health event of a patient, verify the acute health event; and based on the verification of the acute health event, send an alert regarding the acute health event.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

BRIEF DESCRIPTION OF DRAWINGS

Like reference characters refer to like elements throughout the figures and description.

DETAILED DESCRIPTION

Figure 1:
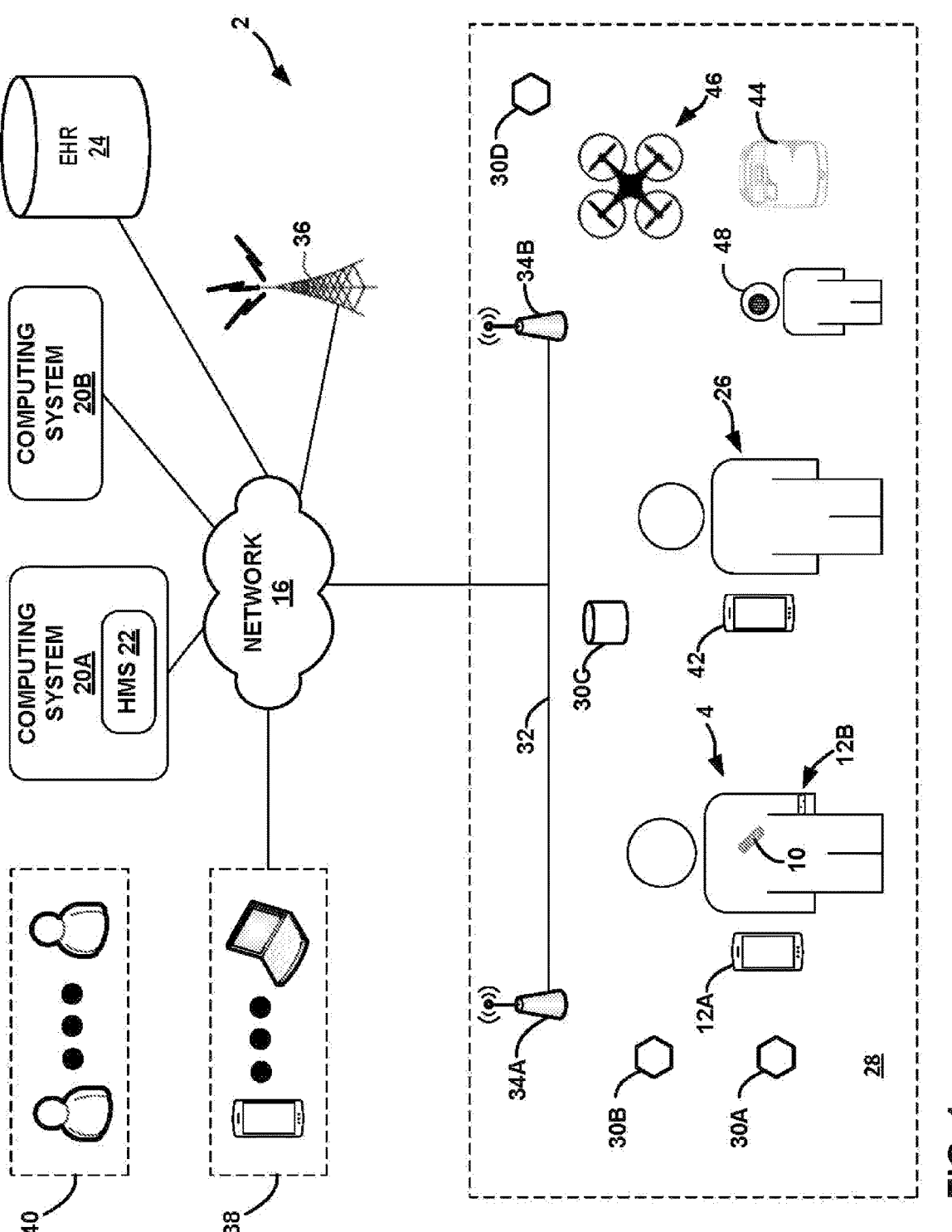
FIG. 1 is a block diagram illustrating an example system configured detect acute health events of a patient, and to respond to such detections, in accordance with one or more techniques of this disclosure.

A patient who is living alone may have an acute health event, such as SCA, stroke, seizure or other epileptic event, hypo/hyperglycemic event, acute myocardial infarction, fall, or anaphylactic shock, and become incapacitated. In the incapacitated state, the patient may not be able to make a phone call to an emergency service, such as 911, to obtain medical help. Since no other person may be around to confirm the medical situation and call the emergency service, the patient may not be able to obtain the medical help that is necessary for the well-being of the patient.

A variety of types of implantable and computing devices are configured detect arrhythmia episodes and other acute health events based on sensed ECGs and, in some cases, other physiological signals. Computing devices that may be used to non-invasively sense and monitor ECGs and other physiological signals include wearable devices with electrodes configured to contact the skin of the patient, such as patches, watches, or necklaces, and other non-contact monitoring devices, such as devices configured to monitor sound, radar, light, images, etc. Such computing devices may facilitate relatively longer-term monitoring of patient health during normal daily activities.

Implantable medical devices (IMDs) also sense and monitor ECGs and other physiological signals, and detect acute health events such as episodes of arrhythmia, cardiac arrest, myocardial infarction, stroke, and seizure. Example IMDs include pacemakers and implantable cardioverter-defibrillators, which may be coupled to intravascular or extravascular leads, as well as pacemakers with housings configured for implantation within the heart, which may be leadless. Some IMDs do not provide therapy, such as implantable patient monitors. One example of such an IMD is the Reveal LINQ™ Insertable Cardiac Monitor (ICM) or the LINQ II™ ICM, available from Medtronic plc, which may be inserted subcutaneously. Such IMDs may facilitate relatively longer-term monitoring of patients during normal daily activities, and may periodically transmit collected data, e.g., episode data for detected arrhythmia episodes, to a remote patient monitoring system, such as the Medtronic Carelink™ Network.

Such an IMD may interact with other devices. The IMD may sense an indication of an acute health event of the patient. These other devices may be verification devices or part of a verification system and may be configured to verify whether the patient actually experienced the sensed acute health event. For example, the verification device or system may verify the acute health event. Based on the verification of the acute health event, the verification device or system or the IMD may send an alert regarding the acute health event, such as call an emergency service. The verification device or system may include at least one of a smartphone, wearable device, video camera, infrared camera, thermal camera, radar system, sonar system, lidar system, bed sensor, smart speaker, smart television, drone, robot, hearing aid(s) or other Internet of Things (IoT) devices.

FIG. 1 is a block diagram illustrating an example system 2 configured detect acute health events of a patient 4, and to respond to such detection, in accordance with one or more techniques of this disclosure. As used herein, the terms "detect," "detection," and the like may refer to detection of an acute health event presently (at the time the data is collected) being experienced by patient 4, as well as detection based on the data that the condition of patient 4 is such that they have a suprathreshold likelihood of experiencing the event within a particular timeframe, e.g., prediction of the acute health event. The example techniques may be used with one or more patient sensing devices, e.g., IMD 10, which may be in wireless communication with one or more patient computing devices, e.g., patient computing devices 12A and 12B (collectively, "computing devices 12"). Computing devices 12 may be verification devices and may attempt to verify the occurrence of an acute health event. Although not illustrated in FIG. 1, IMD 10 include electrodes and other sensors to sense physiological signals of patient 4, and may collect and store sensed physiological data based on the signals and detect episodes based on the data.

In some examples, although not depicted in FIG. 1, patient 4 may have a plurality of patient sensing devices, such as IMD 10. In some examples, the plurality of patient sensing devices may communicate with each other and/or computing device(s) 12. In some examples, the plurality of patient sensing devices may use time matching techniques, such determining a difference in a clock of each patient sensing device and applying the difference when saving a time of a sensed indication of an acute health event, or use a common clock. In this manner, sensed indications of acute health events of different patient sensing devices may be synchronized. In another example, one patient sensing device may be configured as a master and other patient sensing devices may be configured as slaves.

IMD 10 may be implanted outside of a thoracic cavity of patient 4 (e.g., subcutaneously in the pectoral location illustrated in FIG. 1). IMD 10 may be positioned near the sternum near or just below the level of the heart of patient 4, e.g., at least partially within the cardiac silhouette. In some examples, IMD 10 takes the form of the LINQ™ ICM. Although described primarily in the context of examples in which IMD 10 takes the form of an ICM, the techniques of this disclosure may be implemented in systems including any one or more implantable or external medical devices, including monitors, pacemakers, defibrillators, wearable external defibrillators, neurostimulators, or drug pumps. Furthermore, although described primarily in the context of examples including a single implanted patient sensing device, in some examples a system includes one or more patient sensing devices, which may be implanted within patient 4 or external to (e.g., worn by) patient 4.

The example of FIG. 1 includes environment 28. Environment 28 may be a home, office, or place of business, or public venue, as examples. Computing devices 12 are configured for wireless communication with IMD 10. Computing devices 12 retrieve or receive event data and other sensed physiological data from IMD 10 that was collected and stored by the IMD. In some examples, computing devices 12 take the form of personal computing devices of patient 4. For example, computing device 12A may take the form of a smartphone of patient 4, and computing device 12B may take the form of a smartwatch or other smart apparel of patient 4. In some examples, computing devices 12 may be any computing device configured for wireless communication with IMD 10, such as a desktop, laptop, or tablet computer. Computing devices 12 may communicate with IMD 10 and each other according to the Bluetooth®, Bluetooth® Low Energy (BLE), or other wireless communication protocols, as examples. In some examples, only one of computing devices 12, e.g., computing device 12A, is configured for communication with IMD 10, e.g., due to execution of software (e.g., part of a health monitoring application as described herein) enabling communication and interaction with an IMD. In some examples, computing device(s) 12 may be configured to receive an indication of an acute health event of patient 4 from IMD 10.

In some examples, computing device(s) 12, e.g., wearable computing device 12B in the example illustrated by FIG. 1A, may include electrodes and other sensors to sense physiological signals of patient 4, and may collect and store physiological data and detect episodes based on such signals. Computing device 12B may be incorporated into the apparel of patient 14, such as within clothing, shoes, eyeglasses, a watch, ring, necklace, wristband, a hat, etc. In some examples, computing device 12B is a smartwatch or other accessory or peripheral for a smartphone computing device 12A.

One or more of computing devices 12 may be configured to communicate with a variety of other devices or systems via a network 16. For example, one or more of computing devices 12 may be configured to communicate with one or more computing systems, e.g., computing systems 20A and 20B (collectively, "computing systems 20") via network 16. Computing systems 20A and 20B may be respectively managed by manufacturers of IMD 10 and computing devices 12 to, for example, provide cloud storage and analysis of collected data, maintenance and software services, or other networked functionality for their respective devices and users thereof. Computing system 20A may comprise, or may be implemented by, the Medtronic Care-link™ Network, in some examples. In the example illustrated by FIG. 1, computing system 20A implements a health monitoring system (HMS) 22, although in other examples, either of both of computing systems 20 may implement HMS 22. As will be described in greater detail below, HMS 22 facilities detection of acute health events of patient 4 by system 2, and the responses of system 2 to such acute health events.

Computing device(s) 12 may transmit data, including data retrieved or received from IMD 10, to computing system(s) 20 via network 16. The data may include sensed data, e.g., values of physiological parameters measured by IMD 10 and, in some cases one or more of computing devices 12, data regarding episodes of arrhythmia or other acute health events detected by IMD 10 and computing device(s) 12, and other physiological signals or data recorded by IMD 10 and/or computing device(s) 12. HMS 22 may also retrieve data regarding patient 4 from one or more sources of electronic health records (EHR) 24 via network. EHR 24 may include data regarding historical (e.g., baseline) physiological parameter values, previous health events and treatments, disease states, comorbidities, demographics, height, weight, and body mass index (BMI), as examples, of patients including patient 4. HMS 22 may use data from EHR 24 to configure algorithms implemented by IMD 10 and/or computing devices 12 to detect acute health events for patient 4. In some examples, HMS 22 provides data from EHR 24 to computing device(s) 12 and/or IMD 10 for storage therein and use as part of their algorithms for detecting acute health events.

Network 16 may include one or more computing devices, such as one or more non-edge switches, routers, hubs, gateways, security devices such as firewalls, intrusion detection, and/or intrusion prevention devices, servers, cellular base stations and nodes, wireless access points, bridges, cable modems, application accelerators, or other network devices. Network 16 may include one or more networks administered by service providers, and may thus form part of a large-scale public network infrastructure, e.g., the Internet. Network 16 may provide computing devices and systems, such as those illustrated in FIG. 1, access to the Internet, and may provide a communication framework that allows the computing devices and systems to communicate with one another. In some examples, network 16 may include a private network that provides a communication framework that allows the computing devices and systems illustrated in FIG. 1 to communicate with each other, but isolates some of the data flows from devices external to the private network for security purposes. In some examples, the communications between the computing devices and systems illustrated in FIG. 1 are encrypted.

As will be described herein, IMD 10 may be configured to detect acute health events of patient 4 based on data sensed by IMD 10 and, in some cases, other data, such as data sensed by computing devices 12A and/or 12B, and data from EHR 24. In response to detection of an acute health event, IMD 10 may wirelessly transmit an indication of the acute health event, such as a message, to one or both of computing devices 12A and 12B. The message may indicate that IMD 10 detected an acute health event of patient 4. The message may indicate a time that IMD 10 detected the acute health event. The message may include physiological data collected by IMD 10, e.g., data which lead to detection of the acute health event, data prior to detection of the acute health event, and/or real-time or more recent data collected after detection of the acute health event. The physiological data may include values of one or more physiological parameters and/or digitized physiological signals. Some examples of acute health events are cardiac arrest, ventricular fibrillation, ventricular tachycardia, myocardial infarction, pause in heat rhythm (asystole), pulseless electrical activity (PEA), acute respiratory distress syndrome (ARDS), stroke, seizure or other epileptic event, fall, anaphylactic shock, or respiratory failure.

In some examples, any of, or any combination of, computing device(s) 12, Internet of Things (IoT) devices, such as IoT devices 30A-30D (collectively "IoT devices 30"), drone 46, or robot 48 may be verification devices or part of a verification system. The verification device or system may attempt to verify the acute health event. For example, the verification device or system may determine physiological parameters of patient 4 and may determine whether the physiological parameters of the patient meet predefined criteria. The predefined criteria may be indicative of the acute health event.

For example, environment 28 may include a plurality of cameras (e.g., any of IoT devices 30, as well as cameras carried by drone 46 or robot 48). The plurality of cameras may be located throughout a house, for example, and may be used to determine a location of patient 4 and/or to verify the acute health event. In some examples, one or more cameras are only activated by the verification device or system for locating patient 4 or verifying the acute health event in certain instances. For example, a camera may only be activated if the sensed indication of the acute health event is sufficiently strong. For example, strength of the indication may be scored by IMD 10 or computing device(s) 12, and the camera may only be activated if the score is equal to or higher than a predetermined score. In some examples, the score may be probability or risk of the acute health event having occurred or occurring within a certain time.

In some examples, environment 28 includes a house. IoT devices 30 may determine whether patient 4 is inside the house or outside the house. For example, IoT devices 30 may include a smart speaker, e.g., including a microphone or other audio sensor, motion sensor(s), smart lock(s), and/or cameras that may monitor a location of patient 4. Processing circuitry of IoT devices 30, computing devices 12, and/or IMD 10 may determine the location of patient 4 based on the monitoring. The processing circuitry may use the determined location to dispatch drone 46 and/or robot 48 to the location of patient 4. In some examples, the processing circuitry may determine on which floor of building patient 4 is based on such information from IoT devices 30.

In some examples, drone 46 or robot 48 may navigate to the proximity of patient 4 to determine physiological parameters of patient 4. In some examples, cameras may capture video, infrared, thermal, or other images of patient 4. The images may be processed to identify physiological parameters of patient 4. For example, the verification device or system may determine posture and facial features of patient 4 through the use of captured images. In some examples, the verification device or system may use facial recognition techniques on one or more images to detect changes in a face of patient 4, such as a droop, that may be a side effect of a stroke. In some examples, processing circuitry of system 2 may detect and/or confirm a fall based on sensor signals from computing devices 12A or 12B, e.g., accelerometer signals, images captured by cameras, e.g., of IoT devices, drone 46, and/or robot 48, or other sensor signals of such devices.

Infrared cameras, radar systems, sonar systems, lidar systems or other sensors may sense the presence of patient 4 for determining patient location, as well as measure the presence or absence of a pulse, oxygen saturation levels, or breathing of patient 4 when attempting to verify the acute health event. The absence of a pulse, reduced oxygen saturation, the absence of breathing, or convulsions may each be used to verify the acute health event. For example, one of more of IoT devices 30 may be configured to sense heartbeat sounds and the verification device or system may use the heart beat sounds to determine a heartbeat or pulse of patient 4. In some examples, the verification device or system may use radar, lidar, sonar, or cameras to determine respiration rate of patient 4 or changes in surfaces of patient 4, for example, by monitoring changes in the position of chest of patient 4 over time. In some examples, the verification device or system may use a camera to sense blood flow in patient 4 (e.g., using a red-sensitive image of a face of patient 4, or other exposed skin of patient 4). In other examples, the verification device or system may use radar, sonar, or lidar to identify area of interest on patient 4 and analyze a sequence of images from a camera over time to sense blood flow in patient 4. In some examples, the verification device or system may include an oxygen sensor, which may be integrated into computing device 12B, for example, which may be configured to monitor an oxygen saturation level of blood of patient 4. In some examples, the verification device or system may use traditional signal processing or machine learning techniques to combine measurements from multiple sensors to verify the acute health event.

In some examples, in response to the message indicative of the sensing of the acute health event from IMD 10, computing device(s) 12 may prompt patient 4 to provide a response. For example, computing device(s) 12 may audibly ask the patient if they are okay or may ask the patient to provide tactile input indicating that they are okay in an attempt to elicit a response. Computing device(s) 12 may wait for a response from patient 4. After a predetermined period of time, which may be on the order of up to 60 seconds, if the patient had not responded, computing device(s) 12 may attempt to verify the acute health event. For example, computing device 12B may attempt to take a pulse of patient 4.

Other devices in the environment 28 of patient 4 may also be configured to verify the acute health event. For example, environment 28 may include one or more IoT devices, such as IoT devices 30A-30D (collectively "IoT devices 30") illustrated in the example of FIG. 1. IoT devices 30 may include, as examples, so called "smart" speakers, cameras, lights, locks, thermostats, appliances, actuators, controllers, or any other smart home (or building) devices. For example, IoT devices 30 may include video cameras, infrared cameras, thermal cameras, radar systems, sonar system, lidar systems, bed sensors, smart speaker, smart television, hearing aid(s) or other IoT devices, which may include microphones or other sensors for collecting data about patient 4 and/or environment 28. These IoT devices 30 may be configured to determine physiological parameters of patient 4. For example, IoT devices 30 may be configured to determine at least one of pulse rate, blood perfusion, breathing rate, breathing intensity, posture, facial features, color of a face, or an electrocardiogram.

In some examples, IoT devices 30 or computing device(s) 12 may be configured to determine a location of patient 4. For example, a camera may capture an image and image processing techniques may be used to determine that patient 4 is in a captured image. A radar, sonar, or lidar system may transmit radio, sound, or light waves, respectively, and measure reflections of those waves to determine a location of patient 4. Bed sensors may determine that patient 4 is in bed based on pressure placed on the bed sensors. In some examples, computing device(s) 12 may receive, from IoT devices 30, information indicative of the location of patient 4 and may process such information to determine the location of patient 4.

As mentioned above, in some examples, IoT devices 30 may include bed sensors. Bed sensors may be useful in verifying the acute health event as lethal acute health events frequently occur during sleep. In some examples, IoT devices 30 may include a device, such as a camera, that is configured to monitor the behavior of patient 4. For example, the device may capture images of patient 4 and processing circuitry may perform image analysis to determine a location of patient 4 or physiological parameters of patient 4. In some examples, IoT devices 30 may include a device, such as a radar system, that is configured to monitor sleep apnea of patient 4. For example, a radar system, may transmit radio waves and measure reflections of the radio waves to monitor sleep apnea. Reflections of the radio waves may show relatively consistent movement of the chest of patient 4 when breathing normally. Reflections of the radio waves may show more erratic movement of the chest of patient 4 during a sleep apnea episode, where patient 4 may pause breathing and then gasp for air.

In the example of FIG. 1, IoT device 30C is a smart speaker and/or controller, which may include a display. In some examples, rather than computing device(s) 12 attempting to solicit the response from patient 4 or a caregiver, IoT device 30C may attempt to solicit the response. IoT devices 30 may provide audible and/or visual alarms when configured with output devices to do so. As other examples, IoT devices 30 (or computing device(s) 12) may cause smart lights throughout environment 28 to flash or blink or change colors and unlock or open smart locks on doors of the house. By opening smart locks, IoT devices 30 or computing device(s) 12 may facilitate quick entry into the home by EMS personnel or bystander 26. In general, IoT devices 30 may provide visual, audible, or haptic alerts to in order to draw the attention of patient 4, caregivers, family member, bystander, and first responders, e.g., to provide an alert and/or to elicit a response to the alert. In some examples, IoT devices 30 that include cameras or other sensors may activate those sensors to collect data regarding patient 4, e.g., for evaluation or verification of the condition of patient 4 and, in some examples, a location of patient 4.

In some examples, drone 46 may be an unmanned aerial vehicle (UAV). Drone 46 may be equipped with a number of sensors and/or actuators to perform a number of operations, such as determine physiological parameters of patient 4. For example, drone 46 may include a camera or other sensors to navigate to its intended location, identify patient 4 and, in some cases, bystander 26, and to evaluate or verify a condition of patient. In some examples, drone 46 may be configured to determine the location of patient 4, such as through camera images captured by drone 46 or other techniques. In some examples, drone 46 may include user interface devices to communicate with patient 4 and/or bystander 26. In some examples, drone 46 may provide directions to bystander 26, to the location of patient 4 and regarding how to provide first responder care, such as CPR, to patient 4. In some examples, drone 46 may carry medical equipment, e.g., AED 44, and/or medication to the location of patient 4.

In some examples, robot 48 may be equipped with a number of sensors and/or actuators to perform a number of operations, such as determine physiological parameters of patient 4. For example, robot 48 may include a camera or other sensors to navigate to its intended location, identify patient 4 and, in some cases, bystander 26, and to evaluate a condition of patient. In some examples, robot 48 may be configured to determine the location of patient 4, such as through camera images captured by robot 48, audio captured by robot 48, or other techniques. In some examples, robot 48 may include user interface devices to communicate with patient 4 and/or bystander 26. In some examples, robot 48 may provide directions to bystander 26, to the location of patient 4 and regarding how to provide first responder care, such as CPR, to patient 4. In some examples, robot 48 may carry or include medical equipment, e.g., AED 44, and/or medication to the location of patient 4. In some examples, robot 48 may perform a medical intervention on patient 4, such as perform CPR or defibrillation on patient 4, or perform some other medical treatment.

In some examples, in response to the message from IMD 10, computing device(s) 12 may also output an alarm that may be visual and/or audible, and configured to immediately attract the attention of patient 4 or any person in environment 28 with patient 4, e.g., a bystander 26. Computing device(s) 12 may also transmit a message to HMS 22 via network 16. The message may include the data received from IMD 10 and, in some cases, additional data collected by computing device(s) 12 or other devices in response to the detection of the acute health event by IMD 10. For example, the message may include a location of patient 4 determined by computing device(s) 12, IoT devices 30A-30D, drone 46, or robot 48.

Computing device(s) 12 may be configured to wirelessly communicate with IoT devices 30 to cause IoT devices 30 to take the actions described herein. In some examples, HMS 22 communicates with IoT devices 30 via network 16 to cause IoT devices 30 to take the actions described herein, e.g., in response to receiving the alert message from computing device(s) 12 as described above. In some examples, IMD 10 is configured to communicate wirelessly with one or more of IoT devices 30, e.g., in response to detection of an acute health event when communication with computing devices 12 is unavailable or not preferred. In such examples, IoT device(s) 30 may be configured to provide some or all of the functionality ascribed to computing devices 12 herein.

Environment 28 includes computing facilities, e.g., a local network 32, by which IMD 10, computing devices 12, IoT devices 30, and other devices within environment 28 may communicate via network 16, e.g., with HMS 22. For example, environment 28 may be configured with wireless technology, such as 802.11 wireless networks, 802.15 Zig-Bee networks, an ultrawideband protocol, near-filed communication, or the like. Environment 28 may include one or more wireless access points, e.g., wireless access points 34A and 34B (collectively, "wireless access points 34") that provide support for wireless communications throughout environment 28. Additionally or alternatively, e.g., when local network is unavailable, IMD 10, computing devices 12, IoT devices 30, and other devices within environment 28 may be configured to communicate with network 16, e.g., with HMS 22, via a cellular base station 36 and a cellular network.

Computing device(s) 12, and in some examples IoT devices 30, may include input devices and interfaces to allow a user to override the alarm in the event the detection of the acute health event by IMD 10 was false. In some examples, one or more of computing device(s) 12 and IoT device(s) 30 may implement an event assistant. The event assistant may provide a conversational interface or a tactile interface for patient 4 and/or bystander 26 to exchange information with the computing device or IoT device. The event assistant may query the user regarding the condition of patient 4 in response to receiving the alert message from IMD 10. Responses from the user may be used to confirm or override detection of the acute health event by IMD 10, or to provide additional information about the acute health event or the condition of patient 4 more generally that may improve the efficacy of the treatment of patient 4. For example, information received by the event assistant may be used to provide an indication of severity or type (differential diagnosis) for the acute health event. The event assistant may use natural language processing and context data to interpret utterances by the user. In some examples, in addition to receiving responses to queries posed by the assistant, the event assistant may be configured to respond to queries posed by the user. For example, patient 4 may indicate that they feel dizzy and ask the event assistant, "how am I doing?".

In some examples, computing device(s) 12 and/or HMS 22 may implement one or more algorithms to evaluate the sensed physiological data received from IMD 10, and in some cases additional physiological or other data sensed or otherwise collected by the computing device(s) or IoT devices 30, to confirm or override the detection of the acute health event by IMD 10. In some examples, computing device(s) 12 and/or computing system(s) 20 may have greater processing capacity than IMD 10, enabling more complex analysis of the data. In some examples, the computing device(s) 12 and/or HMS 22 may apply the data to a machine learning model or other artificial intelligence developed algorithm, e.g., to determine whether the data is sufficiently indicative of the acute health event.

In examples in which computing device(s) 12 are configured to perform an acute health event confirmation analysis or verification, computing device(s) 12 may transmit alert messages to HMS 22 and/or IoT devices 30 in response to confirming or verifying the acute health event. In some examples, computing device(s) 12 may be configured to transmit the alert messages prior to completing the confirmation or verification analysis, and transmit cancellation messages in response to the analysis overriding the detection of the acute health event by IMD 10. HMS 22 may be configured to perform a number of operations in response to receiving an alert message from computing device(s) 12 and/or IoT device(s) 30. HMS 22 may be configured to cancel such operations in response to receiving a cancellation message from computing device(s) 12 and/or IoT device(s) 30. In some examples, IMD 10 may be configured to transmit alert messages directly to network 16, e.g., via access points 34 or base station 36 without an intervening computing device 12 or IoT device 30. In such examples, HMS 22 may be configured to perform acute health event confirmation analysis or verification in the manner described herein with respect to computing devices 12, IoT devices 30, and other devices.

In some examples, computing device(s) 12 may transmit the alert to a care provider, an emergency medical technician, or other designated persons in environment 28 or near environment 28. For example, the alert may be a communication to the emergency medical technician, or local neighborhood alert system with an automated emergency defibrillator service, to a care provider, etc. In some examples, the alert includes collected data from IMD 10 and the verification device or system, such that medical personnel may be prepared to take quick action on arrival in environment 28. In some examples, the alert includes at least one of a telephone call, a short message service message, an email, a web alert, a security system alert, a social media alert, an audible alert, haptic alert or a visual alert.

In some examples, the verification device or system may send an alert through a security system (which may be one of IoT devices 30) in environment 28 to flash a "save our souls" (SOS) message, sound an audible alarm, or the like. In some examples, the verification device or system may notify neighbors of patient 4 of a medical emergency. In some examples, the verification system may send an alarm or warning to everyone and every device around the environment 28. For example, the verification device or system may send an audible warning to IoT device 30C (the smart speaker), visual alerts via smart lights, and/or haptic alerts via any smartwatch or other smart device, e.g., a bed. In some examples, the verification device or system may send an alarm to a social media group or group email, for example, where there is a geographic or therapy relevance to patient 4.

For example, HMS 22 may be configured to transmit alert messages to one or more computing devices 38 associated with one or more care providers 40 via network 16. Care providers may include emergency medical systems (EMS) and hospitals, and may include particular departments within a hospital, such as an emergency department, catheterization lab, or a stroke response department. Computing devices 38 may include smartphones, desktop, laptop, or tablet computers, or workstations associated with such systems or entities, or employees of such systems or entities. The alert messages may include any of the data collected by IMD 10, computing device(s) 12, and IoT device(s) 30, including sensed physiological parameters, time of the acute health event, location of patient 4, and results of the analysis by IMD 10, computing device(s) 12, IoT device(s) 30, and/or HMS 22. The information transmitted from HMS 22 to care providers 40 may improve the timeliness and effectiveness of treatment of the acute health event of patient 4 by care providers 40. In some examples, instead of or in addition to HMS 22 providing an alert message to one or more computing devices 38 associated with an EMS care provider 40, computing device(s) 12 and/or IoT devices 30 may be configured to automatically contact EMS, e.g., autodial 911 (e.g., in the United States or North America to use the telephone system to contact a 911 call center), in response to receiving an alert message from IMD 10. Again, such operations may be cancelled by patient 4, bystander 26, or another user via a user interface of computing device(s) 12 or IoT device(s) 30, or automatically cancelled by computing device(s) 12 based on a confirmatory analysis or verification performed by the computing device(s) overriding the detection of the acute health event by IMD 10.

Similarly, HMS 22 may be configured to transmit an alert message to computing device 42 of bystander 26, which may improve the timeliness and effectiveness of treatment of the acute health event of patient 4 by bystander 26. Computing device 42 may be similar to computing devices 12 and computing devices 38, e.g., a smartphone. In some examples, HMS 22 may determine that bystander 26 is proximate to patient 4 based on a location of patient 4, e.g., received from computing device(s) 12, and a location of computing device 42, e.g., reported to HMS 22 by an application implemented on computing device 42. In some examples, HMS 22 may transmit the alert message to any computing devices 42 in an alert area determined based on the location of patient 4, e.g., by transmitting the alert message to all computing devices in communication with base station 36.

In some examples, aspects of system 2 may have a social media presence. For example, information regarding the response of bystanders 26 or other responders to an alert generated for patient 4, e.g., the fact that they responded or the speed with which they responded, may be posted to social media accounts for the responder and/or HMS 22. Such a social media presence may encourage responder engagement with system 2. In some examples, the alert message to bystander 26 may be configured to assist a layperson in treating patient. For example, the alert message to bystander 26 may include a location (and in some cases a description) of patient 4, the general nature of the acute health event, directions for providing care to patient 4, such as directions for providing cardio-pulmonary resuscitation (CPR), a location of nearby medical equipment for treatment of patient 4, such as an automated external defibrillator (AED) 44 or life vest, and instructions for use of the equipment. In some examples, computing device(s) 12, IoT device(s) 30, and/or computing device 42 may implement an event assistant configured to use natural language processing and context data to provide a conversational interface for bystander 26. The assistant may provide bystander 26 with directions for providing care to patient 4, and respond to queries from bystander 26 about how to provide care to patient 4.

In some examples, HMS 22 may mediate bi-directional audio (and in some cases video) communication between care providers 40 and patient 4 or bystander 26. Such communication may allow care providers 40 to evaluate the condition of patient 4, e.g., through communication with patient 4 or bystander 26, or through use of a camera or other sensors of the computing device or IoT device, in advance of the time they will begin caring for the patient, which may improve the efficacy of care delivered to the patient. Such communication may also allow the care providers to instruct bystander 26 regarding first responder treatment of patient 4.

In some examples, HMS 22 may control dispatch of a drone 46 to environment 28, or a location near environment 28 or patient 4. Drone 46 may be an unmanned aerial vehicle (UAV). Drone 46 may be equipped with a number of sensors and/or actuators to perform a number of operations. For example, drone 46 may include a camera or other sensors to navigate to its intended location, identify patient 4 and, in some cases, bystander 26, and to evaluate a condition of patient. In some examples, drone 46 may include user interface devices to communicate with patient 4 and/or bystander 26. In some examples, drone 46 may provide directions to bystander 26, to the location of patient 4 and regarding how to provide first responder care, such as CPR, to patient 4. In some examples, drone 46 may carry medical equipment, e.g., AED 44, and/or medication to the location of patient 4.

In some examples, HMS 22 may control dispatch of a robot 48 to environment 28, or a location near environment 28 or patient 4. Robot 48 may be equipped with a number of sensors and/or actuators to perform a number of operations. For example, robot 48 may include a camera or other sensors to navigate to its intended location, identify patient 4 and, in some cases, bystander 26, and to evaluate a condition of patient, such as taking an ECG or measuring a pulse. In some examples, robot 48 may act as an AED by touching two parts of the body of patient 4 with extendable arms having electrodes. In some examples, robot 48 may include user interface devices to communicate with patient 4 and/or bystander 26. In some examples, robot 48 may provide directions to bystander 26, to the location of patient 4 and regarding how to provide first responder care, such as CPR, to patient 4. In some examples, robot 48 may carry medical equipment, e.g., AED 44, and/or medication to the location of patient 4. In some examples, robot 48 may perform a medical intervention on patient 4, such as perform CPR or defibrillation on patient 4, or perform some other medical treatment.

Figure 2:
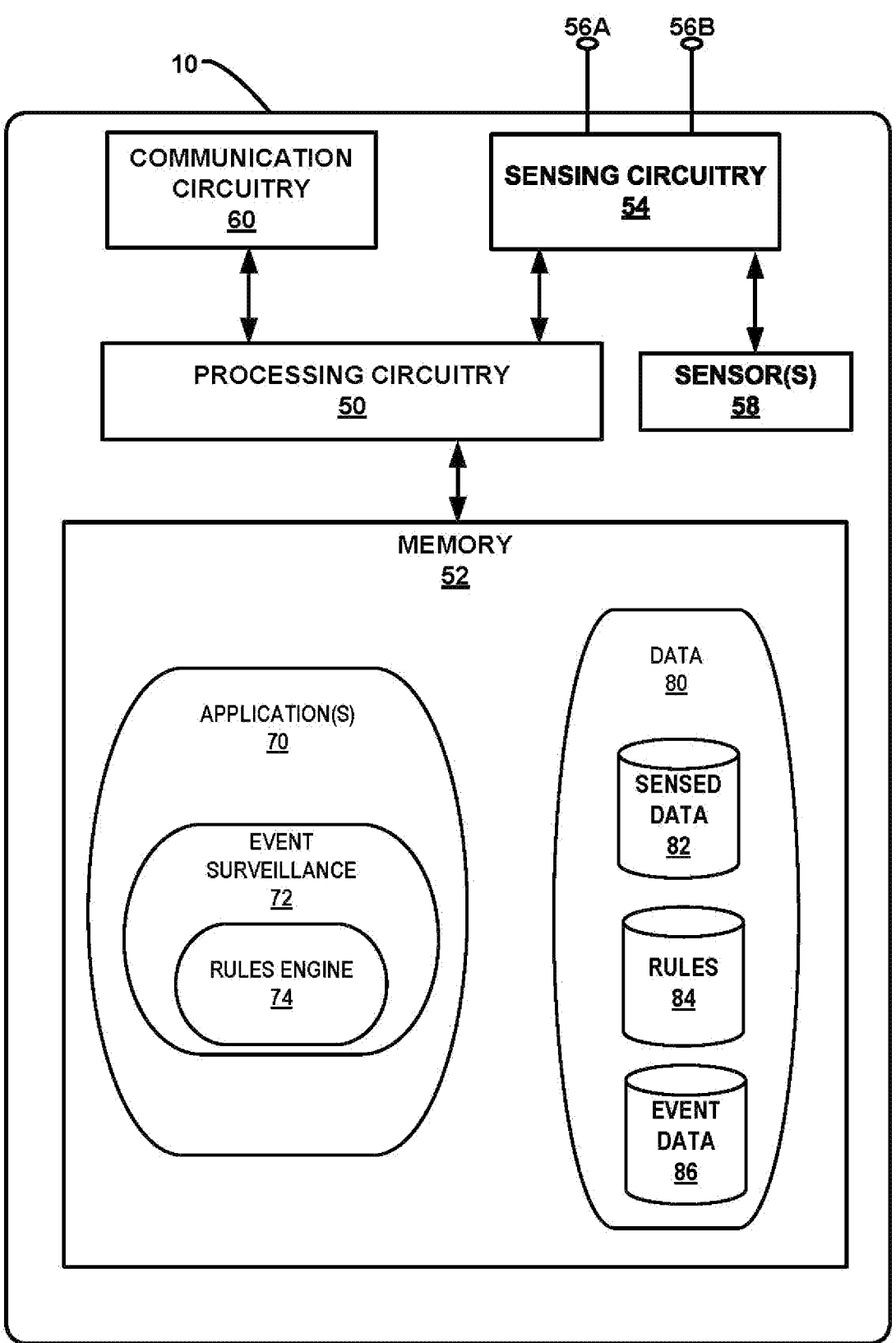
FIG. 2 is a block diagram illustrating an example configuration of a patient sensing device that operates in accordance with one or more techniques of the present disclosure.

FIG. 2 is a block diagram illustrating an example configuration of IMD 10 of FIG. 1. As shown in FIG. 2, IMD 10 includes processing circuitry 50, memory 52, sensing circuitry 54 coupled to electrodes 56A and 56B (hereinafter, "electrodes 56") and one or more sensor(s) 58, and communication circuitry 60.

Processing circuitry 50 may include fixed function circuitry and/or programmable processing circuitry. Processing circuitry 50 may include any one or more of a microprocessor, a controller, a graphics processing unit (GPU), a tensor processing unit (TPU), a digital signal processor (DSP), an application specific integrated circuit (ASIC), a field-programmable gate array (FPGA), or equivalent discrete or analog logic circuitry. In some examples, processing circuitry 50 may include multiple components, such as any combination of one or more microprocessors, one or more controllers, one or more GPUs, one or more TPUs, one or more DSPs, one or more ASICs, or one or more FPGAs, as well as other discrete or integrated logic circuitry. The functions attributed to processing circuitry 50 herein may be embodied as software, firmware, hardware, or any combination thereof. In some examples, memory 53 includes computer-readable instructions that, when executed by processing circuitry 50, cause IMD 10 and processing circuitry 50 to perform various functions attributed herein to IMD 10 and processing circuitry 50. Memory 53 may include any volatile, non-volatile, magnetic, optical, or electrical media, such as a random-access memory (RAM), read-only memory (ROM), non-volatile RAM (NVRAM), electrically-erasable programmable ROM (EEPROM), flash memory, or any other digital media.

Sensing circuitry 54 may monitor signals from electrodes 56 in order to, for example, monitor electrical activity of a heart of patient 4 and produce ECG data for patient 4. In some examples, processing circuitry 50 may identify features of the sensed ECG, such as heart rate, heart rate variability, intra-beat intervals, and/or ECG morphologic features, to detect an episode of cardiac arrhythmia of patient 4. Processing circuitry 50 may store the digitized ECG and features of the ECG used to detect the arrhythmia episode in memory 52 as episode data for the detected arrhythmia episode.

In some examples, sensing circuitry 54 measures impedance, e.g., of tissue proximate to IMD 10, via electrodes 56. The measured impedance may vary based on respiration and a degree of perfusion or edema. Processing circuitry 50 may determine physiological data relating to respiration, perfusion, and/or edema based on the measured impedance.

In some examples, IMD 10 includes sensing circuitry 58, such as one or more accelerometers, microphones, optical sensors, temperature sensors, and/or pressure sensors. In some examples, sensing circuitry 54 may include one or more filters and amplifiers for filtering and amplifying signals received from one or more of electrodes 56 and/or sensors 58. In some examples, sensing circuitry 54 and/or processing circuitry 50 may include a rectifier, filter and/or amplifier, a sense amplifier, comparator, and/or analog-to-digital converter. Processing circuitry 50 may determine physiological data, e.g., values of physiological parameters of patient 4, based on signals from sensors 58, which may be stored in memory 52.

Memory 52 may store applications 70 executable by processing circuitry 50, and data 80. Applications 70 may include an acute health event surveillance application 72. Processing circuitry 50 may execute event surveillance application 72 to detect an acute health event of patient 4 based on combination of one or more of the types of physiological data described herein, which may be stored as sensed data 82. In some examples, sensed data 82 may additionally include data sensed by other devices, e.g., computing device(s) 12, and received via communication circuitry 60. Event surveillance application 72 may be configured with a rules engine 74. Rules engine 74 may apply rules 84 to sensed data 82. Rules 84 may include one or more models, algorithms, decision trees, and/or thresholds. In some cases, rules 84 may be developed based on machine learning.

As examples, event surveillance application 72 may detect a cardiac arrest, a ventricular fibrillation, a ventricular tachycardia, a cardiac pause of asystole, pulseless electrical activity (PEA), or a myocardial infarction based on an ECG and/or other physiological data indicating the electrical or mechanical activity of heart 6 of patient 4 (FIG. 1). In some examples, event surveillance application 72 may detect stroke based on such cardiac activity data. In some examples, sensing circuitry 54 may detect brain activity data, e.g., an electroencephalogram (EEG) via electrodes 56, and event surveillance application 72 may detect stroke or a seizure based on the brain activity alone, or in combination with cardiac activity data or other physiological data. In some examples, event surveillance application 72 detects whether the patient has fallen based on data from an accelerometer alone, or in combination with other physiological data. When event surveillance application 72 detects an acute health event, event surveillance application 72 may store the sensed data 82 that lead to the detection (and in some cases a window of data preceding and/or following the detection) as event data 86.

In some examples, in response to detection of an acute health event, processing circuitry 50 transmits, via communication circuitry 60, event data 86 for the event to computing device(s) 12 (FIG. 1). This transmission may be included in a message indicating the acute health event, as described herein. Transmission of the message may occur on an ad hoc basis and as quickly as possible. Communication circuitry 60 may include any suitable hardware, firmware, software, or any combination thereof for wirelessly communicating with another device, such as computing devices 12 and/or IoT devices 30. In response to receiving the message, computing device(s) 12 may attempt to elicit a response from patient 4 as discussed above with respect to FIG. 1.

Figure 3:
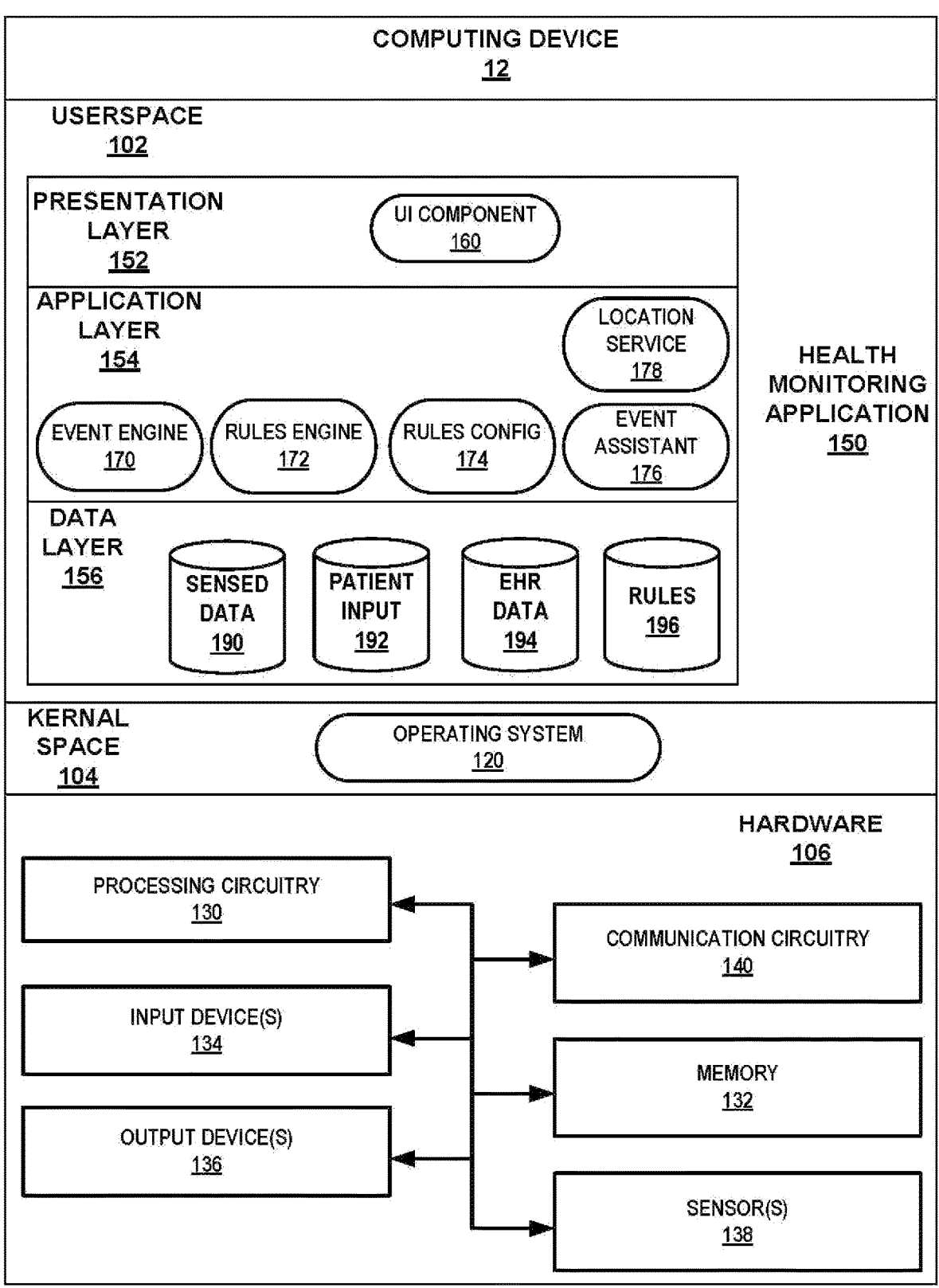
FIG. 3 is block diagram illustrating an example configuration of a computing device that operates in accordance with one or more techniques of the present disclosure.

FIG. 3 is a block diagram illustrating an example configuration of a computing device 12 of patient 4, which may correspond to either (or both operating in coordination) of computing devices 12A and 12B illustrated in FIG. 1. In some examples, computing device 12 takes the form of a smartphone, a laptop, a tablet computer, a personal digital assistant (PDA), a smartwatch or other wearable computing device. In some examples, IoT devices 30, drone 46, and robot 48 may be configured similarly to the configuration of computing device 12 illustrated in FIG. 3.

As shown in the example of FIG. 3, computing device 12 may be logically divided into user space 102, kernel space 104, and hardware 106. Hardware 106 may include one or more hardware components that provide an operating environment for components executing in user space 102 and kernel space 104. User space 102 and kernel space 104 may represent different sections or segmentations of memory, where kernel space 104 provides higher privileges to processes and threads than user space 102. For instance, kernel space 104 may include operating system 120, which operates with higher privileges than components executing in user space 102.

As shown in FIG. 3, hardware 106 includes processing circuitry 130, memory 132, one or more input devices 134, one or more output devices 136, sensing circuitry 138, and communication circuitry 140. Although shown in FIG. 3 as a stand-alone device for purposes of example, computing device 12 may be any component or system that includes processing circuitry or other suitable computing environment for executing software instructions and, for example, need not necessarily include one or more elements shown in FIG. 3.

Processing circuitry 130 is configured to implement functionality and/or process instructions for execution within computing device 12. For example, processing circuitry 130 may be configured to receive and process instructions stored in memory 132 that provide functionality of components included in kernel space 104 and user space 102 to perform one or more operations in accordance with techniques of this disclosure. Examples of processing circuitry 130 may include, any one or more microprocessors, controllers, GPUs, TPUs, DSPs, ASICs, FPGAs, or equivalent discrete or integrated logic circuitry.

Memory 132 may be configured to store information within computing device 12, for processing during operation of computing device 12. Memory 132, in some examples, is described as a computer-readable storage medium. In some examples, memory 132 includes a temporary memory or a volatile memory. Examples of volatile memories include random access memories (RAM), dynamic random access memories (DRAM), static random access memories (SRAM), and other forms of volatile memories known in the art. Memory 132, in some examples, also includes one or more memories configured for long-term storage of information, e.g. including non-volatile storage elements. Examples of such non-volatile storage elements include magnetic hard discs, optical discs, floppy discs, flash memories, or forms of electrically programmable memories (EPROM) or electrically erasable and programmable (EEPROM) memories.

One or more input devices 134 of computing device 12 may receive input, e.g., from patient 4 or another user. Examples of input are tactile, audio, kinetic, and optical input. Input devices 134 may include, as examples, a mouse, keyboard, voice responsive system, camera, buttons, control pad, microphone, presence-sensitive or touch-sensitive component (e.g., screen), or any other device for detecting input from a user or a machine.

One or more output devices 136 of computing device 12 may generate output, e.g., to patient 4 or another user. Examples of output are tactile, audio, and visual output. Output devices 136 of computing device 12 may include a presence-sensitive screen, sound card, video graphics adapter card, speaker, cathode ray tube (CRT) monitor, liquid crystal display (LCD), light emitting diodes (LEDs), or any type of device for generating tactile, audio, and/or visual output.

Sensing circuitry 138 of computing device 12 may sense physiological parameters or signals of patient 4. Sensor(s) 138 may include electrodes, 3-axis accelerometers, an optical sensor, impedance sensors, temperature sensors, pressure sensors, heart sounds sensors, and other sensors, and sensing circuitry (e.g., including an ADC), similar to those described above with respect to IMD 10 and FIG. 2.

Communication circuitry 140 of computing device 12 may communicate with other devices by transmitting and receiving data. Communication circuitry 140 may include a network interface card, such as an Ethernet card, an optical transceiver, a radio frequency transceiver, or any other type of device that can send and receive information. For example, communication circuitry 140 may include a radio transceiver configured for communication according to standards or protocols, such as 3G, 4G, 5G, WiFi (e.g., 802.11 or 802.15 ZigBee), Bluetooth®, or Bluetooth® Low Energy (BLE).

As shown in FIG. 3, health monitoring application 150 executes in user space 102 of computing device 12. Health monitoring application 150 may be logically divided into presentation layer 152, application layer 154, and data layer 156. Presentation layer 152 may include a user interface (UI) component 160, which generates and renders user interfaces of health monitoring application 150.

Application layer 154 may include, but is not limited to, an event engine 170, rules engine 172, rules configuration component 174, event assistant 176, and location service 178. Event engine 170 may be responsive to receipt of an alert transmission from IMD 10 indicating that IMD 10 detected an acute health event. Event engine 170 may control performance of any of the operations in response to detection of an acute health event ascribed herein to computing device 12, such as activating an alarm, transmitting alert messages to HMS 22, controlling IoT devices 30, and analyzing data to confirm or override the detection of the acute health event by IMD 10.

Rules engine 172 analyzes sensed data 190, and in some examples, patient input 192 and/or EHR data 194, to determine whether there is a sufficient likelihood that patient 4 is experiencing the acute health event detected by IMD 10 or to verify that patient 4 has experienced the acute health event detected by IMD 10. Sensed data 190 may include data received from IMD 10 as part of the alert transmission, additional data transmitted from IMD 10, e.g., in "real-time," and physiological parameters and other data related to the condition of patient 4 collected by computing device(s) 12, IoT devices 30, drone 46, and/or robot 48. Rules engine 172 may determine whether the physiological parameters meet predefined criteria to verify the acute health event. As examples sensed data 190 from computing device(s) 12 may include one or more of: activity levels, walking/running distance, resting energy, active energy, exercise minutes, quantifications of standing, body mass, body mass index, heart rate, low, high, and/or irregular heart rate events, heart rate variability, walking heart rate, heart beat series, digitized ECG, blood oxygen saturation, blood pressure (systolic and/or diastolic), respiratory rate, maximum volume of oxygen, blood glucose, peripheral perfusion, and sleep patterns.

Patient input 192 may include responses to queries posed by health monitoring application 150 regarding the condition of patient 4, input by patient 4 or another user, such as bystander 26. The queries and responses may occur responsive to the detection of the event by IMD 10, or may have occurred prior to the detection, e.g., as part long-term monitoring of the health of patient 4. User recorded health data may include one or more of: exercise and activity data, sleep data, symptom data, medical history data, quality of life data, nutrition data, medication taking or compliance data, allergy data, demographic data, weight, and height. EHR data 194 may include any of the information regarding the historical condition or treatments of patient 4 described above. EHR data 194 may relate to history of cardiac arrest, tachyarrhythmia, myocardial infarction, stroke, seizure, chronic obstructive pulmonary disease (COPD), renal dysfunction, or hypertension, history of procedures, such as ablation or cardioversion, and healthcare utilization. EHR data 194 may also include demographic and other information of patient 4, such as age, gender, height, weight, and BMI.

Rules engine 172 may apply rules 196 to the data. Rules 196 may include one or more models, algorithms, decision trees, and/or thresholds. In some cases, rules 196 may be developed based on machine learning. In some examples, rules 196 and the operation of rules engine 172 may provide a more complex analysis of the sensed data received from IMD 10, than is provided by rules engine 74 and rules 84. In some examples, rules 196 include one or more models developed by machine learning, and rules engine 172 applies feature vectors derived from the data to the model(s). For example, rules engine 172 may apply rules 196 to determine whether the physiological parameters captured by IMD 10 and the verification device or system meet predefined criteria to verify the acute health event.

Rules configuration component 174 may be configured to modify rules 196 (and in some examples rules 84) based on feedback indicating whether the detections and confirmations of acute health events by IMD 10 and computing device 12 were accurate. The feedback may be received from patient 4, or from care providers 40 and/or EHR 24 via HMS 22. In some examples, rules configuration component 174 may utilize the data sets from true and false detections and confirmations for supervised machine learning to further train models included as part of rules 196.

As discussed above, event assistant 176 may provide a conversational interface or tactile interface for patient 4 and/or bystander 26 to exchange information with computing device 12. Event assistant 176 may query the user regarding the condition of patient 4 in response to receiving the alert message from IMD 10. Responses from the user may be included as patient input 192. Event assistant 176 may use natural language processing and context data to interpret utterances by the user. In some examples, in addition to receiving responses to queries posed by the assistant, event assistant 176 may be configured to respond to queries posed by the user. In some examples, event assistant 176 may provide directions to and respond to queries regarding treatment of patient 4 from patient 4 or bystander 26.

Location service 178 may determine the location of computing device 12 and, thereby, the presumed location of patient 4. Location service 178 may use global position system (GPS) data, multilateration, and/or any other known techniques for locating computing devices. In some examples, location service 178 may utilize data from other devices to determine the location of patient 4, such as IoT devices 30, drone 46, or robot 48. For example, data from a camera, a radar system, a sonar system, or a lidar system may be used to determine where in environment 28 (FIG. 1) patient 4 is located. In some examples, location service 178 may track where patient 4 is during different times of the day and use the most frequent location at the time of the day that the indication of the acute medical event was sensed as a starting position to determine the location of patient 4. For example, location service 178 may employ one or more of the devices, such as IoT devices 30, drone 46, or robot 48, to check to see if patient 4 is located at the most frequent location for that time of day.

Figure 4:
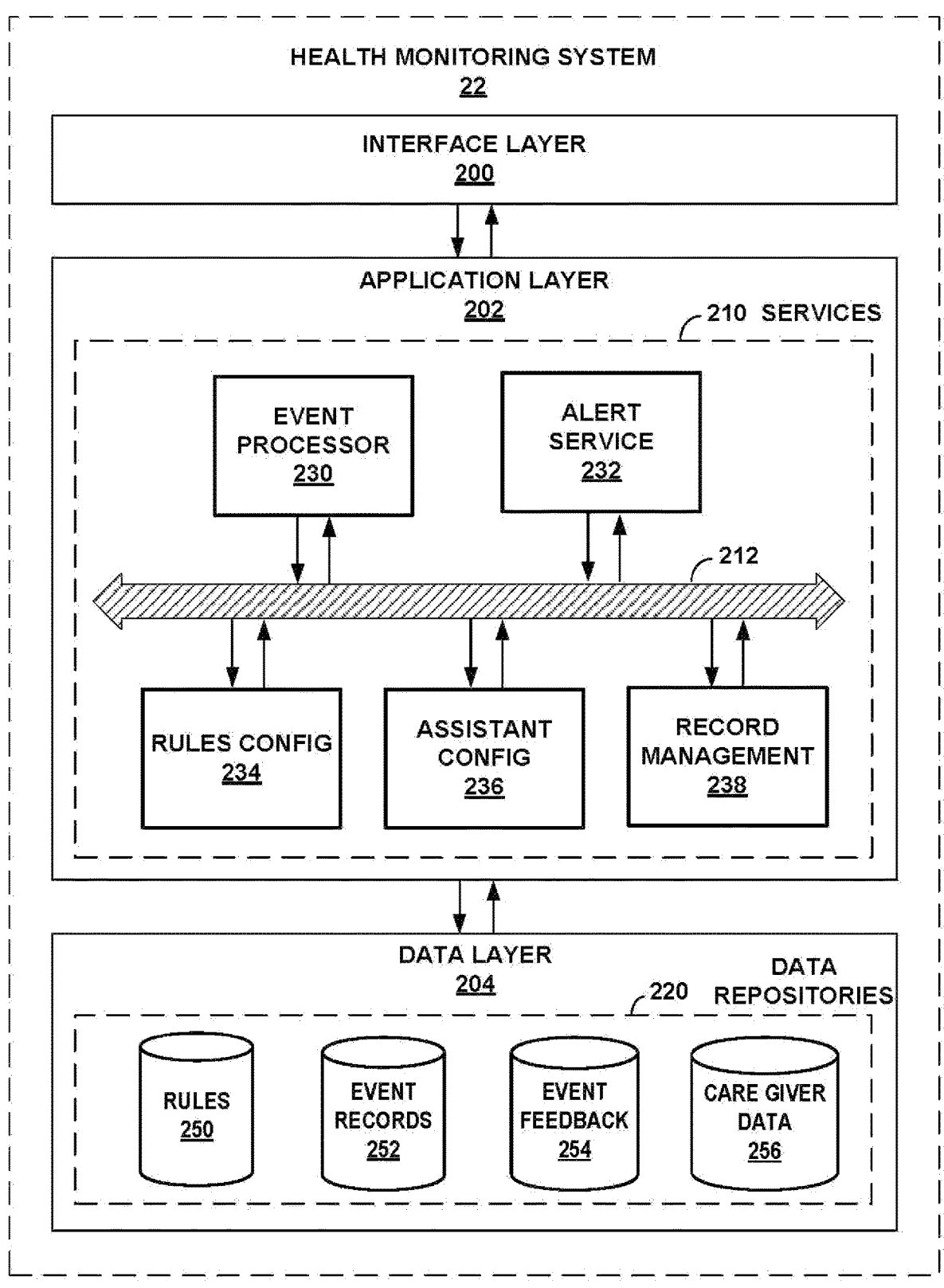
FIG. 4 is a block diagram illustrating an example configuration of a health monitoring system that operates in accordance with one or more techniques of the present disclosure.

FIG. 4 is a block diagram illustrating an operating perspective of HMS 22. HMS 22 may be implemented in a computing system 20, which may include hardware components such as those of computing device 12, embodied in one or more physical devices. FIG. 4 provides an operating perspective of HMS 22 when hosted as a cloud-based platform. In the example of FIG. 4, components of HMS 22 are arranged according to multiple logical layers that implement the techniques of this disclosure. Each layer may be implemented by one or more modules comprised of hardware, software, or a combination of hardware and software.

Computing devices, such as computing devices 12, IoT devices 30, computing devices 38, computing device 42, drone 46, and robot 48 may operate as clients that communicate with HMS 22 via interface layer 200. The computing devices typically execute client software applications, such as desktop application, mobile application, and web applications. Interface layer 200 represents a set of application programming interfaces (API) or protocol interfaces presented and supported by HMS 22 for the client software applications. Interface layer 200 may be implemented with one or more web servers.

As shown in FIG. 4, HMS 22 also includes an application layer 202 that represents a collection of services 210 for implementing the functionality ascribed to HMS herein. Application layer 202 receives information from client applications, e.g., an alert of an acute health event from a computing device 12 or IoT device 30, and further processes the information according to one or more of the services 210 to respond to the information. Application layer 202 may be implemented as one or more discrete software services 210 executing on one or more application servers, e.g., physical or virtual machines. That is, the application servers provide runtime environments for execution of services 210. In some examples, the functionality interface layer 200 as described above and the functionality of application layer 202 may be implemented at the same server. Services 210 may communicate via a logical service bus 212. Service bus 212 generally represents a logical interconnections or set of interfaces that allows different services 210 to send messages to other services, such as by a publish/subscription communication model.

Data layer 204 of HMS 22 provides persistence for information in PPEMS 6 using one or more data repositories 220. A data repository 220, generally, may be any data structure or software that stores and/or manages data. Examples of data repositories 220 include but are not limited to relational databases, multi-dimensional databases, maps, and hash tables, to name only a few examples.

As shown in FIG. 4, each of services 230-238 is implemented in a modular form within HMS 22. Although shown as separate modules for each service, in some examples the functionality of two or more services may be combined into a single module or component. Each of services 230-238 may be implemented in software, hardware, or a combination of hardware and software. Moreover, services 230-238 may be implemented as standalone devices, separate virtual machines or containers, processes, threads or software instructions generally for execution on one or more physical processors.

Event processor service 230 may be responsive to receipt of an alert transmission from computing device(s) 12 and/or IoT device(s) 30 indicating that IMD 10 detected an acute health event of patient and, in some examples, that the transmitting device confirmed or verified the detection. Event processor service 230 may initiate performance of any of the operations in response to detection of an acute health event ascribed herein to HMS 22, such as communicating with patient 4, bystander 26, and care providers 40, activating the verification device or system (e.g., any of IoT devices 30, computing device(s) 12, drone 46, or robot 48) and, in some cases, analyzing data to confirm or override the detection of the acute health event by IMD 10. In some examples, rather than actually verifying the acute health event, the verification device or system may transmit the sensed physiological parameters to HMS 22 and HMS 22 may verify the acute health event.

Record management service 238 may store the patient data included in a received alert message within event records 252. Alert service 232 may package the some or all of the data from the event record, in some cases with additional information as described herein, into one more alert messages for transmission to bystander 26 and/or care providers 40. Care provider data 256 may store data used by alert service 232 to identify to whom to send alerts based on locations of potential bystanders 26 and care providers 40 relative to a location of patient 4 and/or applicability of the care provided by care providers 40 to the acute health event experienced by patient 4.

In examples in which HMS 22 performs an analysis to confirm, verify, or override the detection of the acute health event by IMD 10, event processor service 230 may apply one or more rules 250 to the data received in the alert message, e.g., to feature vectors derived by event processor service 230 from the data. Rules 250 may include one or more models, algorithms, decision trees, and/or thresholds, which may be developed by rules configuration service 234 based on machine learning. Example machine learning techniques that may be employed to generate rules 250 can include various learning styles, such as supervised learning, unsupervised learning, and semi-supervised learning. Example types of algorithms include Bayesian algorithms, Clustering algorithms, decision-tree algorithms, regularization algorithms, regression algorithms, instance-based algorithms, artificial neural network algorithms, deep learning algorithms, dimensionality reduction algorithms and the like. Various examples of specific algorithms include Bayesian Linear Regression, Boosted Decision Tree Regression, and Neural Network Regression, Back Propagation Neural Networks, Convolution Neural Networks (CNN), Long Short Term Networks (LSTM), the Apriori algorithm, K-Means Clustering, k-Nearest Neighbour (kNN), Learning Vector Quantization (LVQ), Self-Organizing Map (SOM), Locally Weighted Learning (LWL), Ridge Regression, Least Absolute Shrinkage and Selection Operator (LASSO), Elastic Net, and Least-Angle Regression (LARS), Principal Component Analysis (PCA) and Principal Component Regression (PCR).

In some examples, in addition to rules used by HMS 22 to confirm acute health event detection, (or in examples in which HMS 22 does not confirm event detection) rules 250 maintained by HMS 22 may include rules 196 utilized by computing devices 12 and rules 84 used by IMD 10. In such examples, rules configuration service 234 may be configured to develop and maintain rules 196 and rules 84. Rules configuration service 234 may be configured to modify these rules based on event feedback data 254 that indicates whether the detections and confirmations of acute health events by IMD 10, computing device 12, and/or HMS 22 were accurate. Event feedback data 254 may be received from patient 4, e.g., via computing device(s) 12, or from care providers 40 and/or EHR 24. In some examples, rules configuration service 234 may utilize event records from true and false detections (as indicated by event feedback data 254) and confirmations for supervised machine learning to further train models included as part of rules 250.

As illustrated in the example of FIG. 4, services 210 may also include an assistant configuration service 236 for configuring and interacting with event assistant 176 implemented in computing device 12 or other computing devices.

Figure 5:
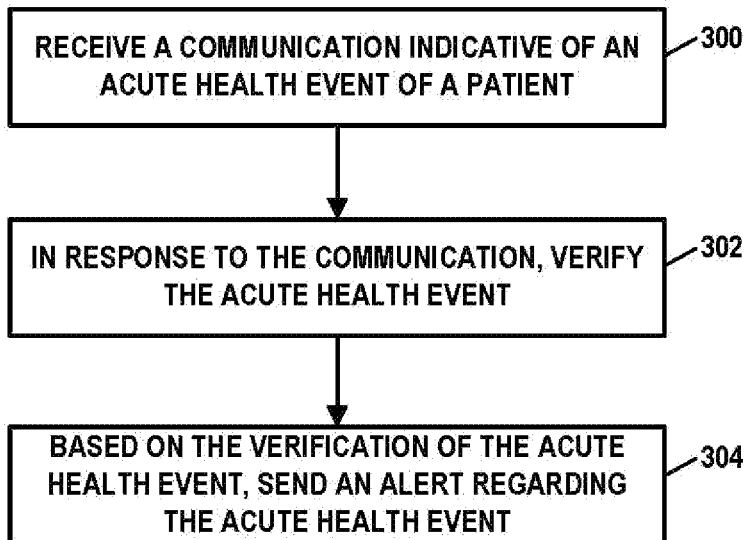
FIG. 5 is a flow diagram illustrating verification techniques according to the present disclosure.

FIG. 5 is a flow diagram illustrating verification techniques according to the present disclosure. Computing device 12A or computing device 12B may receive a communication indicative of an acute health event of patient 4 (300). For example, IMD 10 may monitor physiological parameters of patient 4 and detect an indication of an acute health event of patient 4. Computing device 12A or computing device 12B may receive a communication including an indication of the acute health event from IMD 10.

In response to the communication, computing device 12A or computing device 12B may verify the acute health event (302). For example, computing device 12A or computing device 12B may communicatively connect to any of IoT device(s) 30A-30D, drone 46, and/or robot 48. Computing device 12A or computing device 12B may instruct any of IoT device(s) 30A-30D, drone 46, and/or robot 48 to collect information relating to physiological parameters of patient 4. Computing device 12A or computing device 12B may receive information from at least one of the IoT device, drone, or robot (e.g., the instructed devices) indicative of a verification of the acute health event (e.g., physiological parameters of patient 4). Computing device 12A or computing device 12B may process the information and based on the processed information, confirm the acute health event.

Based on the verification of the acute health event, computing device 12A or computing device 12B may send an alert regarding the acute health event (306). For example, computing device 12A or computing device 12B may send the alert shortly after the verification of the acute health event so as to be close enough to the occurrence of the acute health event to provide an opportunity for successful lifesaving measures to be taken with regard to patient 4. In some examples, the alert includes at least one of a telephone call, a short message service message, an email, a web alert, a security system alert, a social media alert, an audible alert, a visual alert, or a smart device push notification.

In some examples, the received communication is from an implantable medical device. In some examples, computing device 12A or computing device 12B may prompt patient 4 to provide a response. In some examples, the computing device includes a smartphone, a wearable device, or an IoT device. In some examples, the response is at least one of an audible response indicative of the patient not having experienced the acute health event or a tactile response indicative of the patient not having experienced the acute health event. For example, the audible response may be a voice response or other noise response (e.g., a clap). For example, the tactile response may be a button push, fingerprint swipe, touch pad entry, or the like.

In some examples, computing device 12A or computing device 12B may receive information from at least one of IoT device 30A, drone 46, or robot 48 indicative of a verification of the acute health event. In some examples, the received information is from IoT device 30A and IoT device 30A comprises a video camera, an infrared camera, a thermal camera, a radar system, a sonar system, a lidar system, a bed sensor, a smart speaker, or a smart television.

In some examples, based on the verification of the acute health event, computing device 12A or computing device 12B transmit a communication to robot 48 instructing robot 48 to medically intervene with patient 4. In some examples, verifying the acute health event includes determining physiological parameters of patient 4. For example, computing device 12A or computing device 12B may receive information indicative of physiological parameters of patient 4 from any of IoT devices 30, drone 46, or robot 48 and may determine the physiological parameters based on the information. In some examples, the physiological parameters of the patient include at least one of pulse rate, blood perfusion, breathing rate, breathing intensity, posture, facial features, color of a face, or an electrocardiogram. In some examples, verifying the acute health event includes determining whether the physiological parameters of the patient meet predefined criteria. For example, computing device 12A or computing device 12B may determine whether to physiological parameters meet predefined criteria.

In some examples, computing device 12A or computing device 12B may determine a location of patient 4. In some examples, computing device 12A or computing device 12B may open smart locks.

In some examples, the alert includes data indicative of physiological parameters of the patient. In some examples, the acute health event includes at least one of sudden cardiac arrest, stroke, acute myocardial infarction, epilepsy, fall, respiratory failure, or anaphylactic shock.

In the case of fall as an acute health event, for example, IMD 10 may detect that patient 4 has fallen based on, e.g., based on changes or patterns in, one or more signals sensed by sensing circuitry 54 of IMD 10, e.g., via an accelerometer or other sensor(s) 58. Example techniques for detecting fall based on changes in sensor signals are described in commonly-assigned U.S. Patent Application Publication No 2020/0380840, the entire content of which is incorporated herein by reference. In some examples, IMD 10 may determine apply an algorithm, e.g., an ML algorithm, to the one or more signals, or features derived from the signals, to determine a risk of patient 4 falling within a future time period. Example techniques for determining a fall risk are described in commonly assigned U.S. Patent Application Publication No. 2022/0031253, and commonly assigned U.S. Provisional Application No. 63/219,595, filed Jul. 8, 2021, and titled "PREDICTING A LIKELIHOOD OF FALL BASED ON WALKING BUT NOT TALKING," both of which are incorporated herein by reference in their entireties. In such examples, IMD 10 may detect a fall event based on the fall risk exceeding a threshold or otherwise satisfying a criterion. IMD 10 may transmit an alert message and/or other communication to one or more computing devices 12, IoT devices 30, or other devices, e.g., of a verification system, as described herein, based on detecting the fall or fall event. An alert message may be communicated to EMS, caregivers, a hospital, bystanders, and/or other caregivers, as described herein.

Computing devices 12, IoT devices 30, or other devices, as described herein, may verify a fall event. For example, such devices may use accelerometers, microphones or other audio sensors, cameras, and other sensors described herein to confirm that the patient has fallen and/or that the fall requires medical attention. In some examples, processing circuitry 130 of such devices may cancel alerting as described herein if the fall event cannot be confirmed. In some examples, an IoT device 30 of system 2 takes the form of a hearing aid or pair of hearing aids, which may include any of the sensors discussed herein, e.g., microphones and accelerometers, to detect or confirm a fall event. One or more hearing aids may also detect, e.g., based on accelerometer signals, forces likely to result in head trauma or concussion In some examples, processing circuitry 130 of such devices may collect contextual information in response to a fall event via any of the various types of sensors described herein. Processing circuitry 130 may use the contextual information may be used to verify that a fall occurred and determine whether the event requires medical attention. In some examples, processing circuitry 130 may use the contextual information to determine one or more underlying causes of the fall event, or collect such contextual information so that it can be passed along to potential responders to the fall event, e.g., via HMS 22, network 16, and/or ad hoc local wireless networks within environment 28.

The contextual information from various devices may be temporally synchronized or correlated. Examples of contextual information that devices of system 2 may collect in response to a fall include additional ECG or other heart activity data (e.g., sensed by IMD 10 and/or other devices as described herein), blood pressure or perfusion data, image data (e.g., of patient 4 and/or environment 28), or glucose or other blood constituent data. Since there may be a variety of underlying causes of a fall, a variety of the sensor data described herein may be collected in response to detection of a fall event by IMD 10. A cause of the fall event could be determined based on data collected before and after detection of the fall event.

Processing circuitry of system 2 may additionally or alternatively use fall detection and collection of contextual information related to fall detection to confirm a detection of another acute health event, e.g., SCA, by IMD 10. IMD 10 may be configured to detect health events that may cause patient 4 to fall. Consequently, detection of a fall event coincident with the detection of the other health event may be evidence verifying the health event and/or additional information to provide to responders to the health event. In response to detection of a health event by IMD 10, IMD 10, computing devices 12, IoT devices 30, and/or other devices of system 12 may collect data from accelerometers, cameras, and/or other sensors described herein to detect a fall event.

In some examples, processing circuitry of system 2 may respond to an acute health event in a variable manner depending on the type of acute health event and any contextual information associated with the acute health event, e.g., collected by IMD 10 or any other device of system 2 described herein. The responses that may differ in this manner may include whether to transmit an alert to caregivers, responders, bystanders, EMS, or a combination of these, whether to provide alerts via IoT devices, and whether and how to verify the health event detected by IMD 10 using other devices of system 2. These responses may differ based on whether the acute health event is SCA, stroke, seizure or other epileptic event, myocardial infarct, fall. Furthermore, these responses may differ based on contextual data. In the case of detection of a fall by IMD 10, for example, processing circuitry of system 2, e.g., of IMD 10, computing devices 12, or IoT devices 30, may determine whether the fall was preceded by arrhythmia, e.g., based on the ECG sensed by IMD 10. If the fall was preceded by arrhythmia and verified, processing circuitry of system 2 may provide an alert to EMS and other potential responders as described herein. If the fall was not preceded by arrhythmia, processing circuitry of system 2 may not provide an alert to EMS unless the patient remains motionless for predetermined period of time, and may provide a local alert via IoT devices, or otherwise provide an alert to a caregiver or family member.

In some examples, IMD 10 and/or other devices of system 2 may collect any of the sensor data described herein as contextual data of a fall event. For example, IMD 10 may store ECG and activity, posture, or other accelerometer data from before and/or after the detection of the fall event. IMD 10 may provide this contextual data to computing device 12, IoT devices 30, and/or HMS 22. As another example, computing devices 12 and/or IoT devices 30 may prompt patient 4 to verbally (or via other user input) confirm or override the fall detection, and provide any other feedback regarding the fall event. Such data may assist system 2 in verifying the fall event, and any caregiver in treating patient 4, e.g., for any conditions underlying the fall event. For example, ECG data, e.g., heart rate and/or morphology data, may rule in or out arrhythmia or other cardiac causes of the fall event. Processing circuitry of system 2 may also collect trend data of fall events, which may be used to diagnose and/or treat conditions of patient 4 that underlies the falls.

As described herein, system 2 may be configured for detection, verification, and communication of health events of patient 4. In some examples, system 2 may additionally or alternatively be configured to collect clinical data longitudinally from a plurality of patients, such as patient 4. System 2 may provide access to a variety of sources of clinical data, including sensor and location data from IMD 10, computing devices 12, IoT devices 30, drone 46, and robot 48, diary or other data received via from patient 4 via tactile or audio interfaces of computing devices 12 and IoT devices 30, data collected from providers and responders, and data from EHR 24. The clinical data may be collected on behalf of an entity that administers HMS 22 and/or a manufacturer of any of the devices of system 2, such as a manufacturer of IMD 10.

As described herein, patient 4 may be a subscriber of HMS 22, and a client application of HMS 22 may be present on computing device(s) 12 of patient 4. Because the clinical data of patient 4 is sensitive and private, the application may be configured to present, e.g., prompt, patient 4 with an interface to enroll and consent to clinical data collection. The application may be configured such that patient 4 can limit their consent in a variety of ways, such as to certain locations, certain times of day, and certain sources of data and/or types of data from the approved sources. Different sources of data may include IMD 10, computing devices 12, IoT devices 30, drone 46, robot 48, and EHR 24. Some clinical data, e.g., regarding symptoms, diet, and exercise, may be collected via surveys or questionnaires, e.g., as described in U.S. Provisional Application Ser. No. 63/147, 581, filed Feb. 9, 2021, and titled "MEDICAL SURVEY TRIGGER AND PRESENTATION," which is incorporated herein by reference in its entirety.

Figure 6:
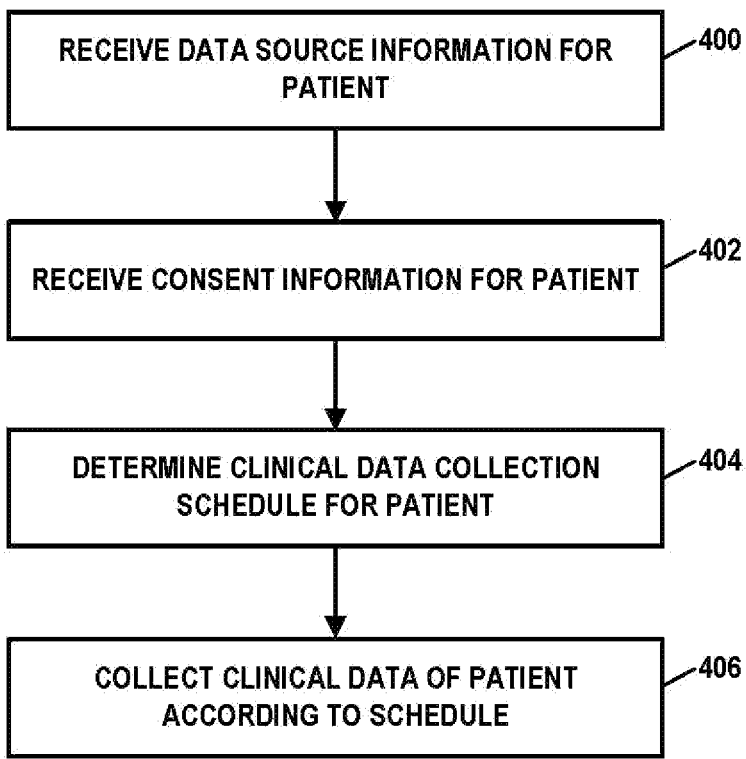
FIG. 6 is a flow diagram illustrating clinical data collection techniques according to the present disclosure.

FIG. 6 is a flow diagram illustrating clinical data collection techniques according to the present disclosure. Although described as being performed by HMS 22, the example technique of FIG. 6 may be performed by processing circuitry of any one or more devices of system 2. For example, one or more computing devices 12 and/or IoT devices 30 may collect clinical data according to the example technique of FIG. 6, and provide the clinical data to HMS 22 or another system for use as described herein.

According to the example technique of FIG. 6, HMS 22 receives data source information for patient 4 (400). The data source information identifies sources of clinical data for patient 4, e.g., identifies computing devices 12, IoT devices 30, and other devices in environment 28. In some examples, patient 4 or a caregiver may manually enter information identifying data sources via one of the devices of patient 4, e.g., computing device 12A. In some examples, one of the devices of patient 4, e.g., computing device 12A, may automatically identify other devices that may be sources of clinical data for patient 4, e.g., using wireless networking discovery techniques. The data source information may be transmitted to HMS 22 via network 16.

HMS 22 may also receive consent information for patient 4 (402). The consent information may include whether patient 4 generally consents to collection of longitudinal clinical data. The consent information may also indicate consent for one or more certain locations, e.g., within environment 28 but not elsewhere, certain times of day, and certain sources of data and/or types of data. Consent may be indicated on a per device basis, e.g., for each of computing devices 12 and/or IoT devices 30, and may be inferred when patient 4 or a caregiver manually identifies the device via the client application for HMS 22. The consent information may be transmitted to HMS 22 via network 16. The consent information may be provided by patient 4, or a caregiver or family member in some examples.

HMS 22 may also determine a clinical data collection schedule for patient 4 based on the data source information and the consent information (404). The clinical data collection schedule for patient 4 may specify the consented times, sources, and types of data for patient 4. An example clinical data collection schedule may specify continuous data collection without limitation to location of patient, for all data types available from a specified list of devices 10, 12, 30, and EHR 24.

HMS 22 may collect longitudinal clinical data of patient 4 according to the determined schedule (406). For example, HMS 22 may send configuration information to devices 10, 12, and 30 that causes the devices to collect longitudinal clinical data of patient 4 according to the determined schedule. HMS 22 may receive the longitudinal clinical data from the devices, e.g., during scheduled, periodic downloads. HMS 22 may also access EHR 24 to retrieve clinical data. HMS 22 may link or correlate the clinical data from the various sources, e.g., by time.

Devices 10, 12, and 30 may collect the clinical data periodically and/or in response to triggers, e.g., health events detected by or other deviations in sensor data sensed by IMD 10. The triggers may be configured by HMS 22 or another user of system 2, e.g., a clinic conducting research based on the clinical data. Prompts for patient, caregiver, or responder information entry may similarly be scheduled, e.g., periodically or based on user-defined triggers. Another example of an event that may trigger collection of clinical data is patient 4 entering or exiting a geofenced area, e.g., a hospital or clinic, as indicated by a location service of a computing device 12.

The entity administering HMS 22 or another entity may use the longitudinal clinical data collected from patient 4 and other patients for a variety of purposes. For example, the longitudinal clinical data may be used to confirm or demonstrate efficacy of system 2 or components thereof in detecting particular health events or otherwise monitoring or treating certain conditions. In some examples, the entity may use the longitudinal clinical data to develop machine learned or other algorithms, e.g., as described herein, to detect health events, such as SCA or fall. Such algorithms may be personalized to patient 4 based on the clinical data of patient 4.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module, unit, or circuit for purposes of clarity, it should be understood that the techniques of this disclosure may be performed by a combination of units, modules, or circuitry associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" or "processing circuitry" as used herein may refer to any of the foregoing structure or any other physical structure suitable for implementation of the described techniques. Also, the techniques could be fully implemented in one or more circuits or logic elements.

The following examples are illustrative of the techniques described herein.

Example 1: A method comprising: receiving, by a verification device, a communication indicative of an acute health event of a patient; in response to the communication, verifying, by the verification device, the acute health event; and based on the verification of the acute health event, sending an alert regarding the acute health event.

Example 2: The method of example 1, wherein the received communication is from an implantable medical device.

Example 3: The method of example 1 or example 2, further comprising: prompting, by the verification device, the patient to provide a response.

Example 4: The method of any one or more of examples 1-3, wherein the verification device comprises a computing device.

Example 5: The method of example 4, wherein the computing device comprises a smartphone, a wearable device, or an Internet of Things device.

Example 6: The method of any one or more of examples 3-5, wherein the response is at least one of an audible response indicative of the patient not having experienced the acute health event or a tactile response indicative of the patient not having experienced the acute health event.

Example 7: The method of any one or more of examples 1-6, further comprising: receiving, by the verification device, information from at least one of an Internet of Things (IoT) device, a drone, or a robot indicative of a verification of the acute health event.

Example 8: The method of example 7, wherein the received information is from an IoT device and the IoT device comprises a video camera, a microphone, an infrared camera, a thermal camera, a radar system, a sonar system, a lidar system, a bed sensor, a smart speaker, or a smart television.

Example 9: The method of any one or more of examples 1-8, further comprising: based on the verification of the acute health event, transmitting a communication to the robot instructing the robot to medically intervene with the patient.

Example 10: The method of any one or more of examples 1-9, wherein verifying the acute health event comprises determining physiological parameters of the patient.

Example 11: The method of example 10, wherein the physiological parameters of the patient comprise at least one of pulse rate, blood perfusion, breathing rate, breathing intensity, posture, facial features, color of a face, or an electrocardiogram.

Example 12: The method of example 10 or example 11, wherein verifying the acute health event comprises determining whether the physiological parameters of the patient meet predefined criteria.

Example 13: The method of any one or more of examples 1-12, further comprising: determining a location of the patient.

Example 14: The method of any one or more of examples 1-13, further comprising: opening, by the verification device, smart locks.

Example 15: The method of any one or more of examples 1-14, wherein the alert comprises at least one of a telephone call, a short message service message, an email, a web alert, a security system alert, a social media alert, an audible alert, a visual alert, a haptic alert, or a smart device push notification.

Example 16: The method of any one or more of examples 1-15, wherein the alert comprises data indicative of physiological parameters of the patient.

Example 17: The method of any one or more of examples 1-16, wherein the acute health event comprises at least one of sudden cardiac arrest, stroke, acute myocardial infarction, epilepsy, fall, respiratory failure, or anaphylactic shock.

Example 18: A device comprising: communication circuitry configured to receive a communication indicative of an acute health event of a patient; memory communicatively coupled to the communication circuitry and being configured to store the indication of the acute health event; and processing circuitry communicatively coupled to the communication circuitry and the memory, the processing circuitry being configured to: in response to the communication, verify the acute health event; and based on the verification of the acute health event, send an alert regarding the acute health event.

Example 19: The device of example 18, wherein the received communication is from an implantable medical device.

Example 20: The device of example 18 or example 19, wherein processing circuitry is further configured to: prompt the patient to provide a response.

Example 21: The device of any one or more of examples 18-20, wherein the device comprises a computing device.

Example 22: The device of example 21, wherein the computing device comprises a smartphone, a wearable device, or an Internet of Things device.

Example 23: The device of any one or more of examples 20-22, wherein the response is at least one of an audible response indicative of the patient not having experienced the acute health event or a tactile response indicative of the patient not having experienced the acute health event.

Example 24: The device of any one or more of examples 18-23, wherein communication circuitry is further configured to: receive information from at least one of an Internet of Things (IoT) device, a drone, or a robot indicative of a verification of the acute health event.

Example 25: The device of example 24, wherein the received information is from an IoT device and the IoT device comprises any one or more of a video camera, an infrared camera, a thermal camera, a radar system, a sonar system, a lidar system, a bed sensor, a smart speaker, or a smart television.

Example 26: The device of any one or more of examples 18-25, further comprising: based on the verification of the acute health event, transmitting a communication to a robot instructing the robot to medically intervene with the patient.

Example 27: The device of any one or more of examples 18-26, wherein verifying the acute health event comprises determining physiological parameters of the patient.

Example 28: The device of example 27, wherein the physiological parameters of the patient comprise at least one of pulse rate, blood perfusion, breathing rate, breathing intensity, posture, facial features, color of a face, or an electrocardiogram.

Example 29: The device of example 27 or example 28, wherein as part of verifying the acute health event, the processing circuitry is configured to determine whether the physiological parameters of the patient meet predefined criteria.

Example 30: The device of any one or more of examples 18-29, wherein the processing circuitry is further configured to: determine a location of the patient.

Example 31: The device of any one or more of examples 18-30, wherein the processing circuitry is further configured to: open smart locks.

Example 32: The device of any one or more of examples 18-31, wherein the alert comprises at least one of a telephone call, a short message service message, an email, a web alert, a security system alert, a social media alert, an audible alert, or a visual alert.

Example 33: The device of any one or more of examples 18-32, wherein the alert comprises data indicative of physiological parameters of the patient.

Example 34. The device of any one or more of examples 18-33, wherein the acute health event comprises at least one of sudden cardiac arrest, stroke, acute myocardial infarction, or anaphylactic shock.

Example 35: The device of any one or more of examples 18-33, wherein the acute health event comprises a fall, and wherein the processing circuitry is configured to collect contextual information from one or more of a camera or a glucose sensor in response to the communication Example 36: A non-transitory computer-readable storage medium storing instructions that, when executed, cause processing circuitry to: in response to receiving a communication indicative of an acute health event of a patient, verify the acute health event; and based on the verification of the acute health event, send an alert regarding the acute health event.

Example 37: A system comprising: processing circuitry; and memory comprising program instructions that, when executed by processing circuitry, cause the processing circuitry to: receive data source information for a patient and consent information for the patient; determine a clinical data collection schedule for the patient based on the data source information and the consent information; and collect clinical data of the patient from a plurality of data sources according to the clinical data collection schedule.

Example 38: The system of example 37, wherein the data source information identifies one or more data source devices of the patient.

Example 39: The system of example 38, wherein the one or more data source devices of the patient comprise one or more of an implantable medical device, a computing device, a wearable device, or an Internet of Things device.

Example 40: The system of example 38 or 39, wherein the one or more data source devices of the patient are identified using wireless networking discovery techniques.

Example 41: The system of any of examples 38-40, wherein, to collect the clinical data of the patient, the processing circuitry is configured to control the one or more data source devices to collect the clinical data according to the clinical data collection schedule for the patient.

Example 42: The system of any of examples 37-41, wherein the consent information indications consent according to one or more of time of day, location, data source, or data type.

Various examples have been described. These and other examples are within the scope of the following claims.

What is claimed is:

1. A device comprising:
communication circuitry configured to receive a communication from an implantable medical device indicative of an acute health event of a patient;
memory communicatively coupled to the communication circuitry and being configured to store the indication of the acute health event; and
processing circuitry communicatively coupled to the communication circuitry and the memory, the processing circuitry being configured to:

in response to the communication, determine physiological parameters of the patient based on values sensed by one or more sensors in another device;

verify the acute health event based on the determined physiological parameters; and based on the verification of the acute health event, send an alert regarding the acute health event, wherein the another device is different than the implantable medical device.

2. The device of claim 1, wherein processing circuitry is further configured to prompt the patient to provide a response.

3. The device of claim 1 wherein the device comprises a computing device.

4. The device of claim 3, wherein the computing device comprises a smartphone, a wearable device, an Internet of Things device.

5. The device of claim 2, wherein the response is at least one of an audible response indicative of the patient not having experienced the acute health event or a tactile response indicative of the patient not having experienced the acute health event.

6. The device of claim 1, wherein the communication circuitry is further configured to receive information from at least one of an Internet of Things (IOT) device, a drone, or a robot, wherein the processing circuitry is configured to verify the acute health event based on the information.

7. The device of claim 6, wherein the received information is from an IoT device and the IoT device comprises at least one of a video camera, audio recording, an infrared camera, a thermal camera, a radar system, a sonar system, a lidar system, a bed sensor, a smart speaker, or a smart television.

8. The device of claim 1, wherein the processing circuitry is further configured to:

based on the verification of the acute health event, control the communication circuitry to transmit a communication to a robot instructing the robot to medically intervene with the patient.

9. The device of claim 1, wherein the physiological parameters of the patient comprise at least one of pulse rate, blood perfusion, breathing rate, breathing intensity, posture, facial features, color of a face, or an electrocardiogram.

10. The device of claim 1, wherein as part of verifying the acute health event, the processing circuitry is configured to determine whether the physiological parameters of the patient meet predefined criteria.

11. The device of claim 1, wherein the processing circuitry is further configured to:

determine a location of the patient.

12. The device of claim 1, wherein the processing circuitry is further configured to:

open smart locks.

13. The device of claim 1, wherein the alert comprises at least one of a telephone call, a short message service message, an email, a web alert, a security system alert, a social media alert, an audible alert, a visual alert, or a haptic alert.

14. The device of claim 1, wherein the alert comprises data indicative of physiological parameters of the patient.

15. The device of claim 1, wherein the acute health event comprises at least one of sudden cardiac arrest, stroke, acute myocardial infarction, or anaphylactic shock.

16. The device of claim 1, wherein the acute health event comprises a fall, and wherein the processing circuitry is configured to collect data from one or more of a camera, a glucose sensor, or a blood pressure sensor in response to the communication.

17. The device of claim 16, wherein the processing circuitry is configured to:

determine whether an arrhythmia preceded the fall; and determine whether to send the alert to a recipient based whether an arrhythmia preceded the fall.

18. A system comprising:

processing circuitry; and memory comprising program instructions that, when executed by processing circuity, cause the processing circuitry to:

receive data source information for a patient and consent information for the patient;

determine a clinical data collection schedule for the patient based on the data source information and the consent information; and collect clinical data of the patient from a plurality of data sources according to the clinical data collection schedule.

19. The system of claim 18, wherein the data source information identifies one or more data source devices of the patient.

20. The system comprising of claim 19, wherein, to collect the clinical data of the patient, the processing circuitry is configured to control the one or more data source devices to collect the clinical data according to the clinical data collection schedule for the patient.

\* \* \* \* \*